US010762636B2

United States Patent
Gering et al.

(10) Patent No.: US 10,762,636 B2
(45) Date of Patent: Sep. 1, 2020

(54) SYSTEMS AND METHODS FOR VOLUMETRIC SEGMENTATION OF STRUCTURES IN PLANAR MEDICAL IMAGES

(71) Applicant: HealthMyne, Inc., Madison, WI (US)

(72) Inventors: David Gering, Waunakee, WI (US); Aaron Avery, Middleton, WI (US); Roger Chylla, Verona, WI (US)

(73) Assignee: HealthMyne, Inc., Madison, WI (US)

( * ) Notice: Subject to any disclaimer, the term of this patent is extended or adjusted under 35 U.S.C. 154(b) by 0 days.

(21) Appl. No.: 15/990,131

(22) Filed: May 25, 2018

(65) Prior Publication Data

US 2019/0005649 A1  Jan. 3, 2019

Related U.S. Application Data

(60) Provisional application No. 62/526,870, filed on Jun. 29, 2017.

(51) Int. Cl.
*G06T 7/00* (2017.01)
*G06T 7/60* (2017.01)
(Continued)

(52) U.S. Cl.
CPC .......... *G06T 7/12* (2017.01); *A61B 6/463* (2013.01); *A61B 6/466* (2013.01); *A61B 6/5217* (2013.01);
(Continued)

(58) Field of Classification Search
None
See application file for complete search history.

(56) References Cited

U.S. PATENT DOCUMENTS

2005/0111710 A1  5/2005 Gritzky et al.
2008/0021502 A1  1/2008 Imielinska et al.
(Continued)

FOREIGN PATENT DOCUMENTS

WO     2010115885 A1   10/2010
WO     WO2017037832 A1   3/2017

OTHER PUBLICATIONS

International Search and Written Opinion for Application No. PCT/US2018/40473 dated Sep. 17, 2018, 15 pages.
(Continued)

*Primary Examiner* — Tize Ma
(74) *Attorney, Agent, or Firm* — Michael Best & Friedrich LLP

(57) ABSTRACT

Methods and systems for volumetric segmentation of structures in planar medical images. One example method includes displaying a first planar medical image. The method further includes receiving a user input indicating a line segment in the first planar medical image. The method also includes determining an inclusion region using the line segment. The inclusion region consists of a portion of the structure. The method further includes determining a containment region using the line segment. The containment region includes the structure. The method also includes determining a background region using the line segment. The background region excludes the structure. The method further includes determining a three dimensional (3D) contour of the structure using the inclusion region, the containment region, and the background region. The method also includes determining a long axis of the structure using the 3D contour. The method further includes outputting a dimension of the long axis.

22 Claims, 11 Drawing Sheets

(51) Int. Cl.

| | |
|---|---|
| G06T 15/08 | (2011.01) |
| G06T 19/20 | (2011.01) |
| G06K 9/62 | (2006.01) |
| G06T 7/12 | (2017.01) |
| G06T 7/13 | (2017.01) |
| G06K 9/20 | (2006.01) |
| A61B 6/00 | (2006.01) |
| G06T 7/11 | (2017.01) |
| G06T 7/62 | (2017.01) |
| G06T 7/194 | (2017.01) |

(52) U.S. Cl.
CPC ......... *G06K 9/2081* (2013.01); *G06K 9/6231* (2013.01); *G06K 9/6278* (2013.01); *G06T 7/0012* (2013.01); *G06T 7/11* (2017.01); *G06T 7/13* (2017.01); *G06T 7/60* (2013.01); *G06T 7/62* (2017.01); *G06T 15/08* (2013.01); *G06T 19/20* (2013.01); *G06K 2209/05* (2013.01); *G06T 7/194* (2017.01); *G06T 2207/10072* (2013.01); *G06T 2207/20104* (2013.01); *G06T 2219/2021* (2013.01)

(56) References Cited

U.S. PATENT DOCUMENTS

| | | | | |
|---|---|---|---|---|
| 2009/0097728 | A1* | 4/2009 | Lee | G06T 7/11 382/131 |
| 2009/0180677 | A1* | 7/2009 | Li | G06T 7/62 382/131 |
| 2015/0078640 | A1 | 3/2015 | Guo et al. | |
| 2015/0089365 | A1 | 3/2015 | Zhao et al. | |
| 2016/0300351 | A1* | 10/2016 | Gazit | G06T 7/11 |
| 2017/0249744 | A1* | 8/2017 | Wang | G06T 7/11 |

OTHER PUBLICATIONS

3D Slicer, Available at: http://www.slicer.org., website available as early as Oct. 18, 2000, 1 page.
Aerts et al., "Decoding tumour phenotype by noninvasive imaging using a quantitative radiomics approach," Nat Commun., 2014; 5(4006): 1-8.
Agam et al., "Vessel tree reconstruction in thoracic CT scans with application to nodule detection," IEEE Transactions on Medical Imaging, 2005; 24(4): 486-499.
Armato et al., "Automated lung segmentation for thoracic CT: Impact on computer-aided diagnosis," Academic Radiology, 2004; 11(9): 1011-1021.
Armato et al., "The lung image database consortium (LIDC) and image database resource initiative (IDRI): a completed reference database of lung nodules on CT scans," Medical physics, 2011; 38(2): 915-931.
Armato III, et al., "Data From LIDC-IDRI," The Cancer Imaging Archive, Available at: http://doi.org/10.7937/K9/TCIA.2015.LO9QL9SX, 2015; 3 pages.
Ben-Cohen et al., "Automated method for detection and segmentation of liver metastatic lesions in follow-up CT examinations," Journal of Medical Imaging, 2015; 2(3): 034502-034502.
Catmull, "A class of local interpolating splines," Computer Aided Geometric Design, 174; 317-326.
Clark et al., "The Cancer Imaging Archive (TCIA): maintaining and operating a public information repository," Journal of digital imaging, 2013; 26(6): 1045-1057.
Cline et al., "3D reconstruction of the brain from magnetic resonance images using a connectivity algorithm," Magnetic Resonance Imaging, 1987; 5(5): 345-352.
Dehmeshki et al., "Segmentation of pulmonary nodules in thoracic CT scans: a region growing approach," IEEE transactions on medical imaging, 2008; 27(4): 467-480.
Diciotti et al., "3-D segmentation algorithm of small lung nodules in spiral CT images," IEEE transactions on Information Technology in Biomedicine, 2008; 12(1): 7-19.
Duda et al., "Pattern classification," John Wiley & Sons, 2001.
Erickson et al., "Radiology Data from The Cancer Genome Atlas Liver Hepatocellular Carcinoma," TCGA-LIHC collection, The Cancer Imaging Archive, Available at: http://doi.org/10.7937/K9/TCIA.2016.IMMQW8UQ, 2016; 3 pages.
Frangi et al., "Multiscale vessel enhancement filtering," Int Conf Med Image Comput Comput Assist Interv., Springer Berlin Heidelberg, 1998; 130-137.
Freedman, "A reality check for IBM's AI ambitions," MIT Technology Review, Available at: https://www.technologyreview.com/s/607965/a-reality-check-for-ibms-ai-ambitions/, 2017; 19 pages.
Gering, "Recognizing Deviations from Normalcy for Brain Tumor Segmentation," MIT Ph.D. Thesis, Available at: http://people.csail.mit.edu/gering/, 2003; 189 pages.
Grady, "Random walks for image segmentation," IEEE transactions on pattern analysis and machine intelligence, 2006; 28(11): 1768-1783.
GrowCut plug-in. Available at: http://www.growcut.com, website available as early as 2008, 2 pages.
Gurcun et al., "Lung nodule detection on thoracic computed tomography images: Preliminary evaluation of a computer-aided diagnosis system," Medical Physics, 2002; 29(11): 2552-2558.
Harris, "Signify Research Market Analysis," http://signifyresearch.net/analyst-insights/quantitative-imaging-software-market-exceed-500m-2021/, 2017, 4 pages.
Holger et al., 2015. A new 2.5 D representation for lymph node detection in CT. The Cancer Imaging Archive. http://doi.org/10.7937/K9/TCIA.2015.AQIIDCNM.
Hu et al., 2001. Automatic lung segmentation for accurate quantitation of volumetric X-ray CT images. IEEE transactions on medical imaging, 20(6), pp. 490-498.
Huttenlocher et al., 1993. Comparing images using the Hausdorff distance. IEEE Transactions on pattern analysis and machine intelligence, 15(9), pp. 850-863.
Invivo DynaCAD, Available at: http://www.invivocorp.com/solutions/lung-cancer-screening/.
Jolly et al., "3D general lesion segmentation in CT," 2008 5th IEEE International Symposium on Biomedical Imaging: From Nano to Macro, Paris, 2008; 796-799.
Kapur, 1999. Model based three dimensional medical image segmentation (Doctoral dissertation, Massachusetts Institute of Technology) 123 pages.
Kotis et al., 2003. Three-dimensional segmentation and growth-rate estimation of small pulmonary nodules in helical CT images. IEEE transactions on medical imaging, 22(10), pp. 1259-1274.
Li, "Markov random field modeling in image analysis," Springer Science & Business Media 2009, 8 pages.
Lung Cancer, Available at: https://www.thoracic.org/patients/patient-resources/breathing-in-america/resources/chapter-11-lung-cancer.pdf, 2010, 12 pages.
Lung-RADS, Available at: https://www.acr.org/Quality-Safety/Resources/LungRADS, website available as early as 2014, 4 pages.
Mirada XD3, Available at: http://www.mirada-medical.com/_public/documents/1425036206_mm3540-1-usaxd3forrecisthr.pdf, 2015; 2 pages.
Nordstrom, "The Quantitative Imaging Network in Precision Medicine," In Tomography, 2016; 2(4): 239-241.
Politi et al., "Lung Cancer in the Era of Precision Medicine," In Clin Cancer Res., 2016; 21(10): 2213-2220.
Press et al. "Numerical recipes 3rd edition: The art of scientific computing," Cambridge university press, 2007; 12 pages.
QIBA CT Volumetry Technical Committee. CT Tumor Volume Change Profile—2016, Consensus Profile. Quantitative Imaging Biomarkers Alliance, Available at: http://qibawiki.rsna.org/index.php/Profiles, See especially "Checklist—CT Tumor Volumetry for Advanced Disease," Nov. 21, 2016; 2 pages.
Ross et al., "Lung extraction, lobe segmentation and hierarchical region assessment for quantitative analysis on high resolution computed tomography images," Med Image Comput Comput Assist Interv., 2009; 12(Pt 2): 690-698.

(56) References Cited

OTHER PUBLICATIONS

Roth et al., "A new 2.5 D representation for lymph node detection using random sets of deep convolutional neural network observations," Int Conf Med Image Comput Comput Assist Interv,Springer, Cham., 2014; 520-527.

Saito et al., "New algorithms for euclidean distance transformation of an n-dimensional digitized picture with applications," Pattern recognition, 1994; 27(11): 1551-1565.

Sato et al., "Three-dimensional multi-scale line filter for segmentation and visualization of curvilinear structures in medical images," Medical image analysis, 1998; 2(2): 143-168.

Seff et al., "Leveraging mid-level semantic boundary cues for automated lymph node detection," Int Conf Med Image Comput Comput Assist Interv,Springer, Cham., 2015; 53-61.

Therasse et al., "New guidelines to evaluate the response to treatment in solid tumors," Journal of the National Cancer Institute, 2000; 92(3): 205-216.

Tunali et al., "P1. 01-041 Quantitative Imaging Features Predict Response of Immunotherapy in Non-Small Cell Lung Cancer Patients," Journal of Thoracic Oncology,2017; 12(1): S474-S475.

Velazquez et al., "Volumetric CT-based segmentation of NSCLC using 3D-Slicer," Scientific reports, 2013; 3(3529): 1-7.

Vezhnevets et al., "GrowCut: Interactive multi-label ND image segmentation by cellular automata," In proc. of Graphicon, 2005; 1(4): 150-156.

Xu et al., "Automated lung nodule segmentation using dynamic programming and EM based classification," In Proc. SPIE, 2002; 4684: 666-676.

Yabroff et al., Economic Burden of Cancer in the US: Estimates, Projections and Future Research, Cancer Epidemiol Biomarkers Prev., 2014; 20(10): 2006-14.

Yan et al., "Semiautomatic segmentation of liver metastases on volumetric CT images," Med Phys. 2015; 42(11): 6283-6293.

Yankeelov et al., "Quantitative Imaging in Cancer Clinical Trials," Clin Cancer Res. 2016; 22(2): 284-290.

Ye et al., "Shape-based computer-aided detection of lung nodules in thoracic CT images," IEEE Transactions on Biomedical Engineering, 2009; 56(7): 1810-1820.

Zhao et al., "Data From RIDER_Lung CT," The Cancer Imaging Archive, Available at: http://doi.org/10.7937/K9/TCIA.2015.U1X8A5NR, 2015; 4 pages.

Zhao et al., "Evaluating variability in tumor measurements from same-day repeat CT scans of patients with non-small cell lung cancer," Radiology. 2009; 252(1): 263-72.

Zhou et al., "Automatic multiscale enhancement and segmentation of pulmonary vessels in CT pulmonary angiography images for CAD applications," Med Phys., 2007; 34(12): 4567-77.

Zhou et al., "Automatic segmentation and recognition of anatomical lung structures from high-resolution chest CT images," Comput Med Imaging Graph., Jul. 2006; 30(5): 299-313.

Zhu et al., "An effective interactive medical image segmentation method using fast growcut. In MICCAI workshop on interactive medical image computing," Int Conf Med Image Comput Comput Assist Interv., 2014; 1-9.

Zou et al., "Statistical validation of image segmentation quality based on a spatial overlap index," Academic radiology, 2004; 11(2): 178-189.

Gering, "Semi-automatic Brain Tumor Segmentation by Drawing Long Axes on Multi-plane Reformat" Pre-Conference Proceedings of the 7th MICCAI BraTS Challenge, pp. 153-160, Sep. 2018.

International Search Report and Written Opinion for Application No. PCT/US2019/059897 dated Jan. 22, 2020 (14 pages).

\* cited by examiner ial Application No. 62/526,870, entitled "SYSTEMS AND METHODS FOR ANALYZING MEDICAL IMAGES," filed Jun. 29, 2017, the entire contents of which is incorporated herein by reference.

FIELD

Embodiments of the disclosure relate to planar medical images and, more particularly, to using a system and method for identifying, delineating, and segmentation of structures in planar medical images.

BACKGROUND

In the diagnosis and treatment of certain human diseases by medical imaging, clinicians seek to make certain measurements and delineate the boundaries of certain structures (for example, cancer lesions, tumors, etc.) and normal organs in the body. The measurements are subject to the expert interpretation of a trained radiologist, but are suggested by patterns of contrast contained in planar medical images. Oncologists seek more quantitative measurements such as faster review times, better capturing of volumes, masses, etc. from the radiologists. Lesion delineation can be a source of uncertainly, since typically, the lesion delineation process involves an experienced physician, interpreting, and manually contouring computed tomography (CT) alone or combined with position emission tomography (PET) imaging, on a slice-by-slice basis. As a result, advanced quantitative metrics and automation are needed for the trained professionals reviewing the medical images. Current tools are too slow for the radiologists to provide these metrics for the oncologists on all patients.

SUMMARY

The disclosure provided herein allows a clinician to interactively define and visualize certain artifacts such as segmentation, the long axis, and the short axis. The segmentation of planar medical images is important in medical diagnosis because segmentation provides information associated to anatomical structures as well as potential abnormal tissues necessary to treatment planning and patient follow-up.

One embodiment provides a method for volumetric segmentation of a structure in a plurality of planar medical images. The method includes receiving, at an electronic processor, the plurality of planar medical images. The plurality of planar medical images form a three dimensional (3D) volume that includes the structure. The method also includes displaying, on a display, a first planar medical image from the plurality of planar medical images. The method further includes receiving, with a user interface, a user input indicating a line segment in the first planar medical image. The method also includes determining, with the electronic processor, an inclusion region of the 3D volume using the line segment. The inclusion region consists of a portion of the structure. The method further includes determining, with the electronic processor, a containment region of the 3D volume using the line segment. The containment region includes the structure. The method also includes determining, with the electronic processor, a background region of the 3D volume using the line segment. The background region excludes the structure. The method further includes determining, with the electronic processor, a 3D contour of the structure using the inclusion region, the containment region, and the background region. The method also includes determining, with the electronic processor, a long axis of the structure using the 3D contour of the structure. The method further includes outputting a dimension of the long axis of the structure with the electronic processor.

Another embodiment provides a system for determining volumetric segmentation of a structure in a plurality of planar medical images. The system includes a display, a user interface, and an electronic processor. The electronic processor is configured to receive the plurality of planar medical images. The plurality of planar medical images form a 3D volume that includes the structure and a plurality of voxels. The electronic processor is also configured to display, on the display, a first planar medical image from the plurality of planar medical images. The electronic processor is further configured to receive, with the user interface, a user input indicating a line segment in the first planar medical image. The electronic processor is also configured to determine an inclusion region of the 3D volume using the line segment. The inclusion region consists of a portion of the structure. The electronic processor is further configured to determine a containment region of the 3D volume using the line segment. The containment region includes the structure. The electronic processor is also configured to determine a background region of the 3D volume using the line segment. The background region excludes the structure. The electronic processor is further configured to classify voxels located within the containment region as belonging to either a foreground class or a background class using the inclusion region, the containment region, and the background region. The electronic processor is also configured to determine a 3D contour of the structure based on a border in the 3D volume between the voxels belonging to the foreground class and the voxels belonging to the background class. The electronic processor is further configured to determine a long axis of the structure using the 3D contour of the structure. The electronic processor is also configured to output a dimension of the long axis of the structure.

Yet another embodiment provides a non-transitory machine-readable storage medium for use in connection with a system that includes an electronic processor, a display, and a user interface. The non-transitory machine-readable storage medium includes instructions that when executed by the electronic processor cause the electronic processor to receive a plurality of planar medical images. The plurality of planar medical images forms a 3D volume that includes a structure. The instructions also cause the electronic processor to display, on the display, a first planar medical image from the plurality of planar medical images. The instructions further cause the electronic processor to receive, with the user interface, a user input indicating a line segment in the first planar medical image. The instructions also cause the electronic processor to determine an inclusion region of the 3D volume using the line segment. The inclusion region consists of a portion of the structure. The instructions further cause the electronic processor to determine a containment region of the 3D volume using the line segment. The containment region includes the structure. The instructions also cause the electronic processor to determine a background region of the 3D volume using the line segment. The background region excludes the structure. The instructions further cause the electronic processor to determine a 3D contour of the structure using the inclusion region, the containment region, and the background region. The instructions also cause the electronic processor to determine a long axis of the structure using the 3D contour of the structure. The instructions further cause the electronic processor to output a dimension of the long axis of the structure.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
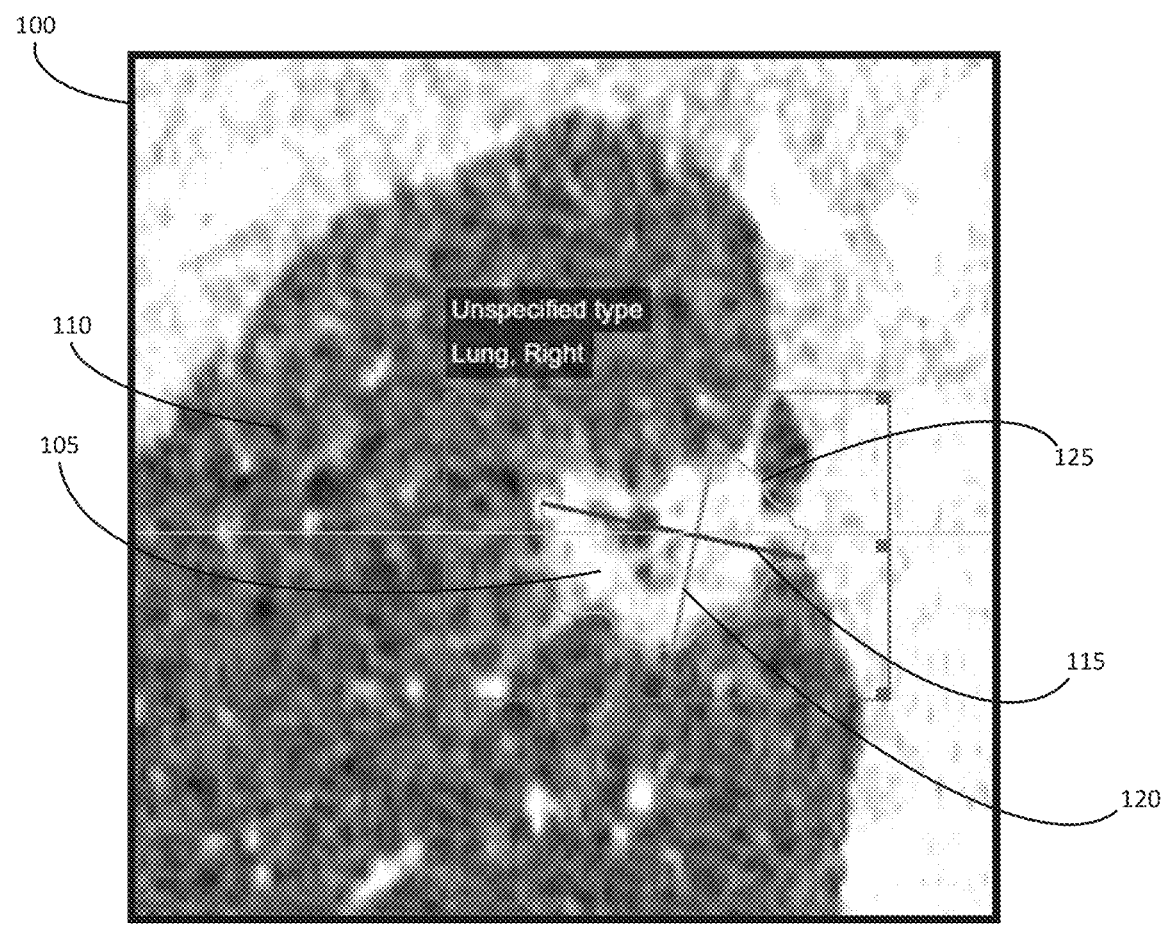
FIG. 1 is a planar medical image including visual indicators for a long axis, a short axis, and a two dimensional (2D) contour of a structure, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Before any embodiments of the disclosure are explained in detail, it is to be understood that the disclosure is not limited in its application to the details of construction and the arrangement of components set forth in the following description or illustrated in the accompanying drawings. The disclosure is capable of other embodiments and of being practiced or of being carried out in various ways.

Radiological scans generate a stack of image slices considered to form an image volume. A medical image dataset could be a single volume, such as a Computed Tomography (CT) scan. Or it could be a set of several volumes, such as a Magnetic Resonance (MR) scan. Multi-spectral MR scans the patient several times using different scanning protocols which highlight various type of tissue types. For example, edema can be distinguished by its darker appearance on a T1-weighted image and brighter appearance on a T2-weighted image. A medical image dataset could also be a fusion of multiple imaging modalities, such as a CT scan with Positron Emission Tomography (PET). By aligning multi-modal image volumes, the functional information conveyed by the PET can be understood in the context of the anatomic information conveyed by the CT. Digital Imaging and Communications in Medicine (DICOM) is a standard for handling, storing, printing, and transmitting information in medical imaging. DICOM includes a file format definition and a network communications protocol.

FIG. 1 is an example planar medical image 100 of a lesion 105 in a lung 110. The lesion 105 includes a long axis 115, a short axis 120, and a two dimensional (2D) contour 125. The 2D contour 125 delineates the boundary of the lesion 105.

Radiologists traditionally read medical image datasets on a slice-by-slice basis. Not long ago, radiologists viewed images on films on a light box. Image assessments were qualitative and any quantitative measurements of structures had to be simple such as length from placing a ruler on the image. Modern technology has digitized the process and now, doctors can read images displayed on computers, also known as a Picture Archiving and Communication Systems (PACS). The PACS systems have the capability of showing the images in one of three planes, axial, sagittal, or coronal. Multi Plane Reformat (MPR) can present simultaneous image views of all three planes. However, the workflow still follows the traditional process of reading it slice-by-slice instead of treating it as a 3D volume. Therefore any quantitative measurements, even when using a PACS workstation, are still confined to single slices.

Standard measurements of structures in planar medical images include the long axis and the short axis. The long axis is the longest one dimensional line segment of a structure in one planar medical image in which the structure is the longest. The long axis does not refer to the true longest 3D segment, but rather the longest axis identified within the plane of a planar medical image. The short axis is defined as the diameter that is perpendicular to the long axis on the same slice as the long axis. The short axis is the longest one dimensional line segment in same plane of the planar medical image containing the long axis. The short axis can have a length less than or equal to the long axis depending upon the circularity of the structure.

The long and short axis measurements serve as the building blocks for computing standard metrics for tracking the progress of a disease. For example, one commonly used standard is Response Evaluation Criteria in Solid Tumors (RECIST) that is used to monitor the response to therapy. Another example is Lung CT Screening Reporting and Data (Lung-RADS), which is a quantitative score that is used to measure the extent and progression of lung lesions. Both these measurements rely upon the long axis and short axis calculations.

An emerging field of interest to the medical imaging community is Radiomics. Radiomics is the discovery of correlation between lesion phenotypes and quantifiable image metrics. On a given lesion, hundreds of quantitative measurements are possible such as intensity, shape, and texture. These measurements can be combined to yield a Radiomics "signature," i.e., an imaging biomarker.

The fundamental requirement for extracting the image metrics is the ability to perform a volumetric segmentation of the image set. One method of calculating the volume is for the radiologist to manually delineate the boundaries of the lesion on each slice where it appears. This is a time-consuming task that no radiologist can fit into their fast paced workflow. What is needed is a method for computing volumetric segmentation that is as fast and easy for a radiologist as drawing a long axis and the short axis. A study of semi-automated segmentation using state-of-the-art research software (described by Rios-Velazquez, E., Parmar, C., Jermoumi, M., Mak, R. H., van Baardwijk, A., Fennessy, F. M., . . . Aerts, H. J. W. L. (2013). Volumetric CT-based segmentation of NSCLC using 3D-Slicer. *Scientific Reports*. Online publication. doi:10.1038/srep03529, the entire contents of which is incorporated herein by reference) show that it still takes approximately 10 minutes to produce the volumetric segmentation of a lung lesion.

In some embodiments, systems and methods described herein provide a semi-automated segmentation process where the user's interaction closely mimics the process of drawing the long axis. Dragging the end point of an axis directly influences the 3D volume segmentation. The work flow provided herein is not only fast, but also very familiar to the radiologists as they are very accustomed to measuring diameters. The process ensures flexibility. The system and methods described herein produce volumetric segmentation of a lung lesion in approximately one minute or less.

Figure 2:
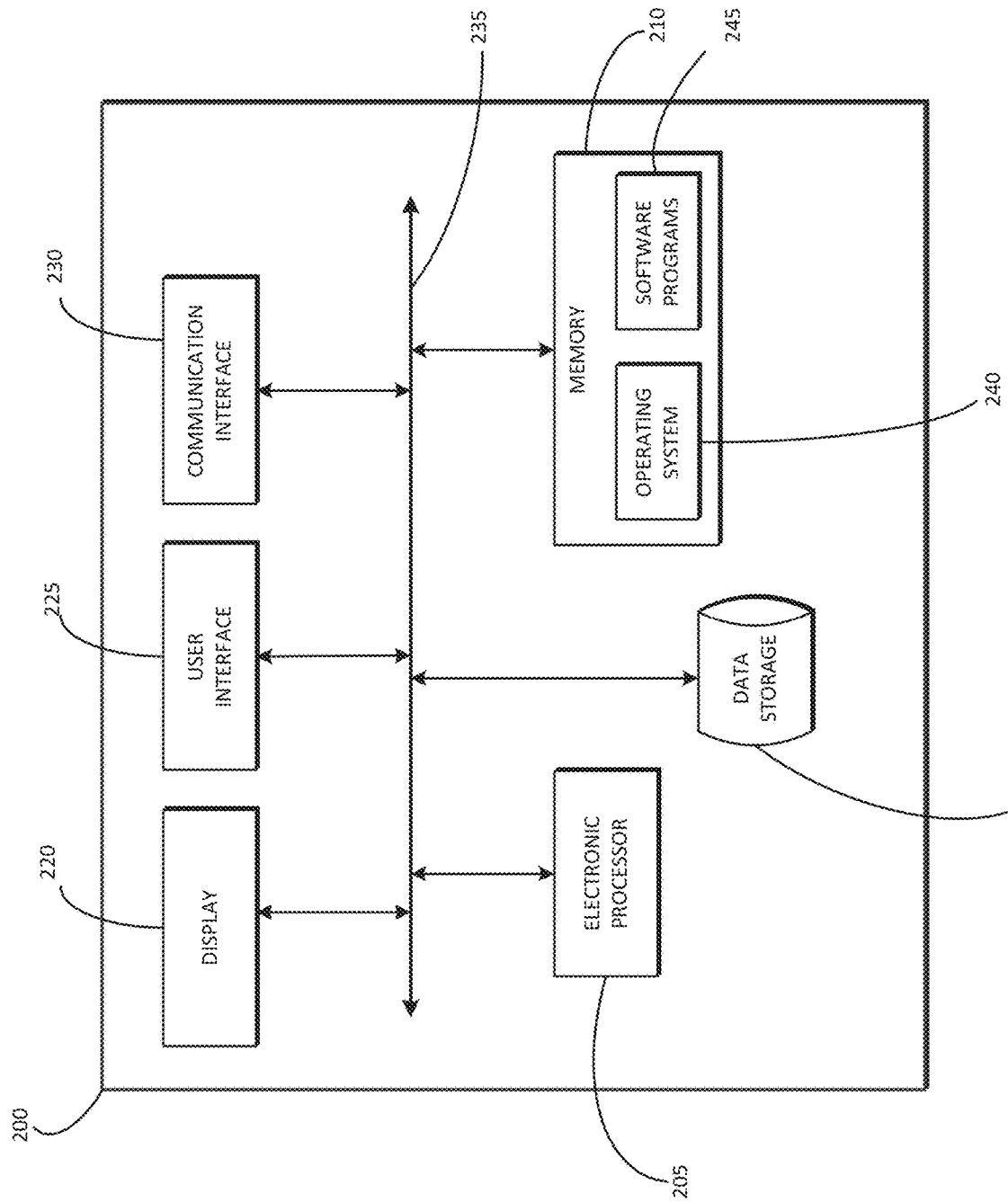
FIG. 2 is a diagram of a system for determining volumetric segmentation of structures in planar medical images, in accordance with some embodiments.

FIG. 2 is a diagram an example system 200 for determining volumetric segmentation of structures in planar medical images. The system 200 may combine hardware, software, and firmware, to implement methods described herein. In the embodiment illustrated in FIG. 2, the system 200 includes an electronic processor 205, a memory 210, a data storage 215, a display 220, a user interface 225, a communication interface 230, and a bus 235. In some embodiments, the system 200 includes fewer or additional components in configurations different from the one illustrated in FIG. 2. For example, in some embodiments, the system 200 includes multiple electronic processors, displays, or combinations thereof.

The electronic processor 205 may include at least one processor or microprocessor that interprets and executes a set of instructions stored, for example, in the memory 210.

The memory 210 may include volatile memory elements (for example, random access memory (RAM)), nonvolatile memory elements (for example, ROM), and combinations thereof. The memory 210 may have a distributed architecture, where various components are situated remotely from one another, but may be accessed by the electronic processor 205. The memory 210 may include an operating system 240 and software programs 245. The software programs 245 may be configured to implement the methods described herein. The memory 210 may also store temporary variables or other intermediate information used during the execution of instructions by the electronic processor 205.

The data storage 215 may include a non-transitory, tangible, machine-readable storage medium that stores machine-readable code or instructions. In one example, the data storage 215 stores a set of instructions detailing the methods described herein that when executed by the electronic processor 205 cause the electronic processor 205 to perform the methods. The data storage 215 may also include a database or a database interface for storing an application module. In some embodiments, the data storage 215 is located external to the system 200.

The display 220 is a suitable display, for example, a liquid crystal display (LCD) touch screen, or an organic light-emitting diode (OLED) touch screen. In some embodiments, the system 200 implements a graphical user interface (GUI) (for example, generated by the electronic processor 205, using the operating system 240 stored in the memory 210, and presented on the display 220), that enables a user to interact with the system 200.

The user interface 225 can include any combination of digital and analog input devices required to achieve a desired level of control for the system 200. In some embodiments, the user interface 225 includes one or more electronic devices for receiving user input such as a keyboard, a mouse, a trackpad, and the like. Alternatively or in addition, the user interface 225 includes a touch sensitive interface. For example, in some embodiments, the display 220 is a touch-screen display that receives user input using detected physical contact (for example, detected capacitance or resistance). Based on user input, the display 220 outputs signals to the electronic processor 205 which indicate positions on the display 220 currently being selected by physical contact. In some embodiments, the user interface 225 is located external to the system 200.

The communication interface 230 provides the system 200 a communication gateway with an external network (for example, a wireless network, the Internet, etc.). The communication interface 230 may include, for example, an Ethernet card or adapter or a wireless local area network (WLAN) card or adapter (for example, Institute of Electrical and Electronic Engineers standard 802.11 a/b/g/n). The communication interface 230 may include address, control, and/or data connections to enable appropriate communications on the external network.

The bus 235, or other component interconnection, may permit communication among the components of the system 200. The bus 235 may be, for example, one or more buses or other wired or wireless connections, as is known in the art. The bus 235 may have additional elements, which are omitted for simplicity, such as controllers, buffers (for example, caches), drivers, repeaters and receivers, or other similar components, to enable communications. The bus 235 may also include address, control, data connections, or a combination of the foregoing to enable appropriate communications among the aforementioned components.

Figure 3:
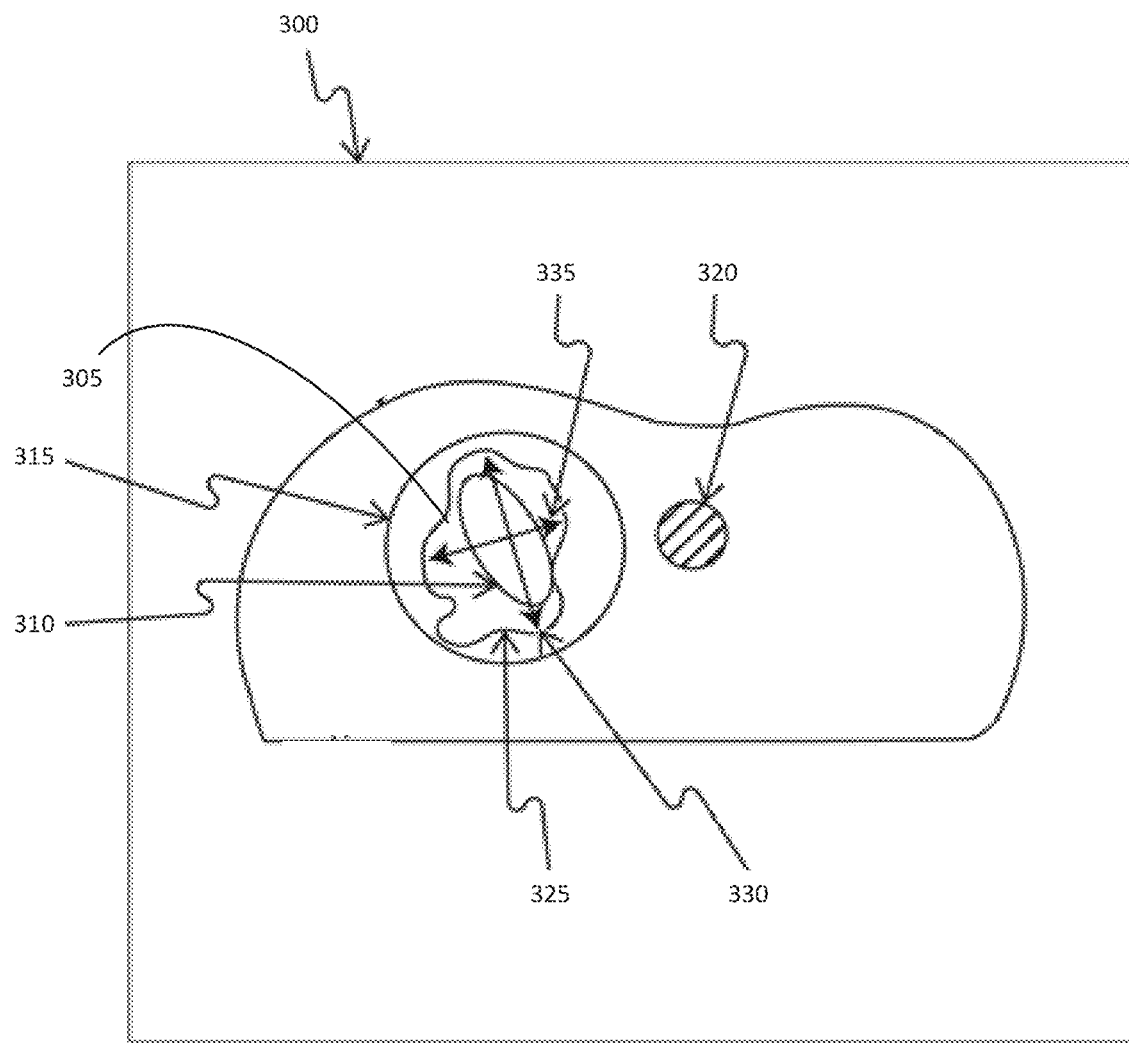
FIG. 3 is a planar medical image including an inclusion region, a containment region, and a background region, in accordance with some embodiments.

FIG. 3 illustrates an example planar medical image 300 showing a structure 305. FIG. 3 includes an inclusion region 310 (shown in FIG. 3 at as an ellipse). The inclusion region 310 is positioned completely within the structure 305 such that the inclusion region 310 includes at least a portion of the structure 305. FIG. 3 also includes a containment region 315 (shown in FIG. 3 as a circle). The containment region 315 is positioned such that it includes the entirety of the structure 305. FIG. 3 also includes a background region 320 (shown in FIG. 3 as a circle). The background region 320 is positioned such that it does not include any portion of the structure 305.

As will be described in more detail below, the system 200 initially determines the inclusion region 310, the containment region 315, and the background region 320. In some embodiments, the sizes and positions of the inclusion region 310, the containment region 315, and the background region 320 can later be manipulated by the user. As will be described in more detail below, the system 200 uses the inclusion region 310, the containment region 315, and the background region 320 perform a volumetric segmentation of the structure 305. In other words, the system 200 uses the inclusion region 310, the containment region 315, and the background region 320 to determine a three dimensional (3D) contour 325 of the structure 305. The system 200 also determines a long axis 330 of the structure 305 and a short axis 335 of the structure 305 using the inclusion region 310, the containment region 315, the background region 320, the 3D contour 325, or a combination thereof.

Figure 4:
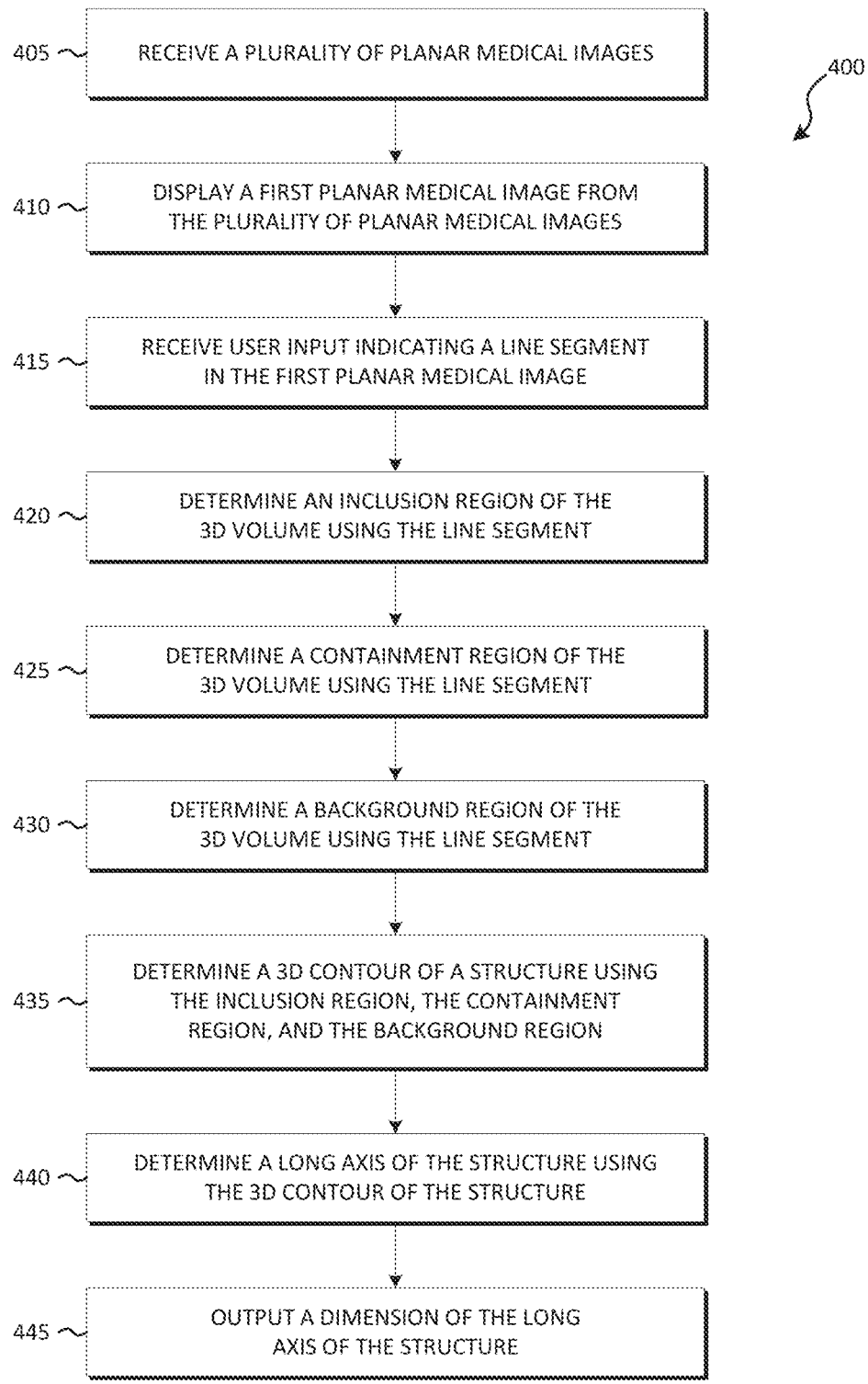
FIG. 4 is a flowchart of a method for determining volumetric segmentation of a structure in a plurality of planar medical images, in accordance with some embodiments.

FIG. 4 illustrates an example method 400 for performing volumetric segmentation of a structure in a plurality of planar medical images. The method 400 is described with respect to FIGS. 2 and 3. The method 400 is described as being performed by the system 200 and, in particular, the electronic processor 205. However, it should be understood that in some embodiments, portions of the method 400 may be performed by other devices included in the system 200.

At block 405, the electronic processor 205 receives a plurality a planar medical images. The plurality of planar medical images forms a 3D volume that includes the structure 305. The plurality of planar medical image includes, for example, one or more computed tomography (CT) images, positron emission tomography (PET) images, magnetic resonance imaging (MRI) images, X-ray images, or a combination thereof. In some embodiments, the system 200 imports the plurality of planar medical images from a computer network (for example, a server) or a file system. In some embodiments, the imported medical images includes one or more of a set of CT, PET, multi-spectral MRI images all of which define the Image Pixel and Image Plane module of the DICOM PS 3.3 specification and are assembled to create a 3D rectilinear image volume.

At block 410, the electronic processor 205 displays one of the plurality of planar medical images (for example, a first planar medical image) on the display 220.

At block 415, the electronic processor 205 receives user input from the user interface 225 indicating a line segment in the first planar medical image. In some embodiments, the line segment is a straight line. In alternate embodiments, the line segment is a non-straight line. The line segment is an approximation of the long axis by the user that is drawn through a stroke gesture across the first planar medical image with a pointing device (for example, a cursor). In some embodiments, the user interface 225 detects a user selection at one location in the first planar medical image (for example, a first location), and subsequently detects a user deselection at a different location in the first planar medical image (for example, a second location). The electronic processor 205 then determines the line segment as a line between the first location and the second location.

In the some embodiments, a user selection includes the user interface 225 receiving a selection signal generated by a user input device. For example, the user interface 225 receives a selection signal generated by a mouse responsive to a user clicking a button on the mouse or generated by a keyboard responsive to a user clicking a key on the keyboard. In such embodiments, the electronic processor 205 may store the location of a cursor on the display 220 as the first location when the selection signal is received. Alternatively or in addition, the user selection includes physical contact with the display 220. For example, the user selection includes a user touching the display 220 with their finger. In such embodiments, the electronic processor 205 may store the location of the initial physical contact on the display 220 as the first location.

In the some embodiments, the user deselection includes a termination of the selection signal generated by a user input device. For example, the user deselection may include the user releasing a button on a mouse or releasing a key on a keyboard. In such embodiments, the electronic processor 205 may store the location of the cursor on the display 220 as the second location when the termination of the selection signal is detected. Alternatively or in addition, the user deselection includes the termination of physical contact with the display 220. For example, the user deselection includes the user removing their finger from the display 220. In such embodiments, the electronic processor 205 may store the location of the latest physical contact on the display 220 as the second location when the user removes their finger.

Returning to FIG. 4, at block 420, the electronic processor 205 determines an inclusion region 310 of the 3D volume using the line segment. The inclusion region 310 includes only the structure 305 and, in the most usual cases, only a portion of the structure 305. The line segment describes the size of the structure 305 along one dimension and the initial layout of the inclusion region 310 may be an oblong region oriented along the line segment. In some embodiments, the electronic processor 205 determines the size of the structure 305 along other dimensions by analyzing orthogonal scout planes given statistical sampling along the line segment. For example, the electronic processor 205 may use probability distributions that are modeled parametrically (for example, as Gaussian Mixture Models (GMMs)) based on the line segment while determining the inclusion region 310.

At block 425, the electronic processor 205 determines a containment region 315 of the 3D volume using the line segment. The containment region 315 includes all of the structure 305. The initial layout of the containment region 315 may be more spherical than the inclusion region 310. The containment region 315 may be automatically constrained to circumscribe the inclusion region 310. In some embodiments, the electronic processor 205 determines three 2D contours of the structure using the line segment. Each of the three 2D contours is in a different plane of the 3D volume. For example, the electronic processor 205 determines a first 2D contour for an axial plane of the 3D volume, a second 2D contour for a sagittal plane of the 3D volume, and a third 2D contour for a coronal plane of the 3D volume. Next, the electronic processor 205 determines the containment region 315 as an ellipsoid in the 3D volume that completely encompasses the three 2D contours. The inclusion region 310 may be reshaped such that each of its three intersections with the three planes is inscribed in the 2D contour associated with that plane. In some embodiments, the electronic processor 205 determines the 2D contours using probability distributions (for example, Gaussian) for image brightness derived from statistical sampling along the line segment. Alternatively or in addition, the electronic processor 205 determines the 2D contours using samples of boundary profiles that may be determined based on the end points of the line segment.

At block 430, the electronic processor 205 determines a background region 320 of the 3D volume using the line segment. The background region 320 excludes the structure. The initial layout of the background region 320 may be to a location outside the containment region 315 that has low probability of belonging to the structure 305. In some embodiments, the electronic processor 205 determines the background region 320 by searching the vicinity outside the containment region 315, and within the body outline, while maximizing the Mahalanobis distance from the inclusion region 310. Intentionally seeking statistical separation between the background region 320 and the inclusion region 310 is more effective than placing the background region 320 based on spatial criteria alone.

In some embodiments, the electronic processor 205 determines more than one background region of the 3D volume. Multiple background regions allow sampling of disparate objects. For example, the electronic processor 205 may determine initial layouts of two background regions by selecting locations with intensities both above and below those of the inclusion region 310.

At block 435, the electronic processor 205 determines a 3D contour 325 of the structure 305 using the inclusion region 310, the containment region 315, and the background region 320. The 3D volume includes a plurality of voxels. Each voxel is a unit of graphic information that defines a point in the 3D volume. As will be described in more detail below, the electronic processor 205 classifies voxels in the plurality of voxels as belonging to either a foreground class or a background class.

The voxels in the 3D volume that make up the structure 305 belong to the foreground class. The other voxels in the 3D volume belong to the background class. The electronic processor 205 classifies voxels (for example, a first set of voxels) located within the inclusion region 310 as belonging to the foreground class. The electronic processor 205 classifies voxels (for example, a second set of voxels) located within the background region 320 as belonging to the background class.

To classify voxels (for example, a third set of voxels) located within the containment region 315 and outside the inclusion region 310, the electronic processor 205 statistically samples all (or a portion) of the plurality of voxels. The voxels located within the inclusion region 310 (i.e., the first set of voxels) statistically typify the foreground class. The voxels located within the background region 320 (i.e., the second set of voxels) statistically typify the background class. In some embodiments, the electronic processor 205 statistically samples the first set of voxels and the second set of voxels to classify the third set of voxels. Alternatively or in addition, the electronic processor 205 statistically samples the voxels located within the containment region 315 and the voxels located within the background region 320 to classify the third set of voxels.

In some embodiments, the electronic processor 205 classifies the third set of voxels using Bayesian classification wherein prior probabilities are spatially varying and derived from region boundaries and may be a function of the distance from the inclusion region 310 and the containment region 315. In some embodiments, the electronic processor 205 uses the voxels located within the inclusion region 310 and the voxels located within the background region 320 to perform Parzen windowing to estimate the likelihoods for Bayesian classification. Conditional densities (for example, likelihoods) may be derived from a function of the histogram of the voxels in each region. Noise and artifacts in the planar medical images vary greatly by dose level and choice of reconstruction kernel. Thus, in some embodiments, the electronic processor 205 augments Bayesian classification with Markov Random Fields and with at least three iterations of a mean-field approximation. In order to achieve a smoothly varying structure, the electronic processor 205 may perform regularization. Examples of regularization processing include connected component analysis (for example, remove islands and fill holes), morphological operations (for example, dilation, erosion, opening, and closing), active contours (for example, snakes and level sets), and fitting a 3D mesh to the voxel classification by adapting vertices connected by virtual springs to their neighbors to provide a regularizing force that smoothes the surface. Super-sampling the image voxel data is another way to produce smoother results, especially since medical image voxels tend to have anisotropic shape.

The voxels assigned to the foreground class define the boundary of the structure 305. After classifying each of the plurality of voxels as belonging to the foreground class or the background class, the electronic processor 205 determines a border in the 3D volume between the voxels belonging to the foreground class and the voxels belonging to the background class. The electronic processor 205 may determine a 3D contour 325 of the structure 305 based on this border. For example, the electronic processor 205 may determine the 3D contour 325 of the structure 305 to be the border between the voxels belonging to the foreground class and the voxels belonging to the background class.

As described herein, the structure 305 is wholly contained with the containment region 315. As such, some (or all) of the voxels located outside the containment region 315 may not be relevant to defining the 3D contour 325 of the structure 305. Thus, in some embodiments, the electronic processor 205 does not classify every voxel of the plurality of voxels as belonging to the foreground class or the background class when determining the 3D contour 325 of the structure 305. For example, the electronic processor 205 may only classify voxels located within the inclusion region 310 (i.e., the first set of voxels), voxels located within the background region 320 (i.e., the second set of voxels), voxels located within the containment region 315 and outside the inclusion region 310 (i.e., the third set of voxels), or a combination thereof. In general, the 3D volume can include a large quantity of voxels (for example, about 100 million voxels). Classifying every single voxel in the 3D volume requires a lot of processor power and processor time to complete. By not classifying every voxel in the 3D volume, the electronic processor 205 is able to determine the 3D contour 325 of the structure 305 much faster.

As described herein, the containment region 315 is used to narrow the region of interest in the 3D volume. However, the containment region 315 is not the same as a bounding box. In general, bounding boxes are manually drawn by users. As such, bounding boxes are much larger than necessary and have no orientation. On the other hand, as described herein, the containment region 315 is determined based on 2D contours of the structure 305. As such, the containment region 315 is shaped to more accurately represent the region of interest than a bounding box.

Returning to FIG. 4, at block 440, the electronic processor 205 determines a long axis 330 of the structure 305 using the 3D contour 325 of the structure 305. In some embodiments, the electronic processor 205 determines the long axis 330 of the structure 305 for the plurality of planar medical images. For example, the electronic processor 205 determines the long axis 330 of the structure 305 as the longest one dimensional line segment that is present in all of the plurality of planar medical images. In other words, the electronic processor 205 identifies the planar medical image with the longest one dimensional line segment and sets the long axis 330 as this line segment. Alternatively or in addition, the electronic processor 205 determines the long axis 330 of the structure 305 for a specific planar medical image. For example, the electronic processor 205 determines the long axis 330 of the structure 305 as the longest one dimensional line segment that is present in a single, specific planar medical image.

At block 445, the electronic processor 205 outputs a dimension of the long axis 330 of the structure 305. A dimension (for example, a first dimension) of the long axis 330 of the structure 305 may include a measurement of the length of the long axis 330, a position of the long axis 330, a specific planar medical image that includes the long axis 330, or a combination (or derivative) thereof. In some embodiments, the electronic processor 205 outputs the dimension of the long axis 330 by transmitting data indicating the dimension via the communication interface 230. For example, the electronic processor 205 may transmit data via the communication interface 230 indicating the length of the long axis 330. Alternatively or in addition, the electronic processor 205 outputs the dimension of the long axis 330 by storing data indicating the dimension. For example, the electronic processor 205 may store data indicating the length of the long axis 330 in the memory 210, the data storage 215, or both. Alternatively or in addition, the electronic processor 205 outputs the dimension of the long axis 330 by displaying the dimension on the display 220. For example, the electronic processor 205 may cause the display 220 to display a visual indicator of the long axis 330 on a planar medical image (as illustrated in FIG. 3). As a further example, the electronic processor 205 may cause the display 220 to display the length of the long axis 330.

In some embodiments, the electronic processor 205 determines a short axis 335 of the structure 305 using the 3D contour 325 of the structure 305. In some embodiments, the electronic processor 205 determines the short axis 335 of the structure 305 as the longest one dimensional line segment perpendicular to the long axis 330 in the same planar medical image as the long axis 330. In some embodiments, the electronic processor 205 outputs a dimension (for example, a second dimension) of the short axis 335 of the structure 305. For example, the electronic processor 205 may cause the display 220 to display a visual indicator of the short axis 335 on a planar medical image (as illustrated in FIG. 3).

In some embodiments, the electronic processor 205 causes the display 220 to display a visual indication of the 3D contour 325. For example, display 220 may display a boundary delineating the 3D contour 325 of the structure 305 on a planer medical image (as illustrated in FIG. 3).

Figure 5:
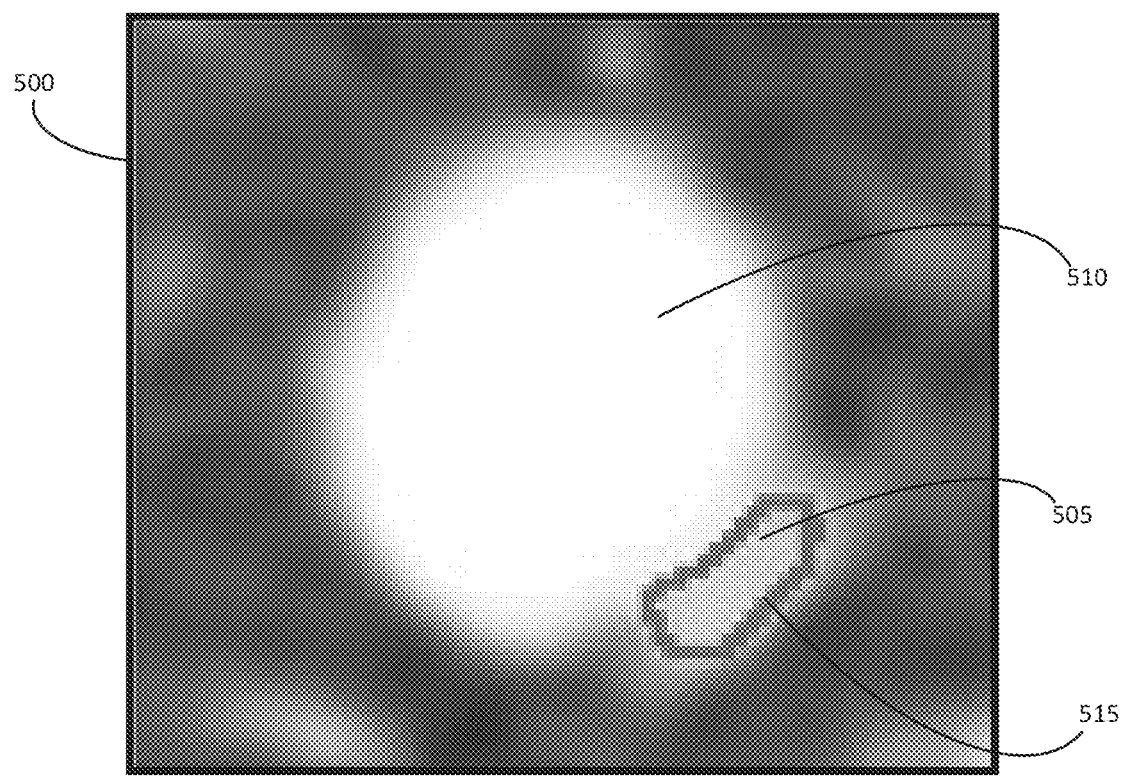
FIG. 5 is a planar medical image including an avoidance region, in accordance with some embodiments.

In some situations, a structure of interest (for example, a tumor or lesion) may be located near a different structure. For example, FIG. 5 is planar medical image 500 of a blood vessel 505 positioned near a nodule 510. The blood vessel 505 is positioned close enough to the nodule 510 such that the electronic processor 205 may inadvertently determine the blood vessel 505 to be part of the nodule 510 when performing volumetric segmentation of the nodule 510. Thus, in some embodiments, the electronic processor 205 determines an avoidance region 515 to separate nearby structures that are not part of the structure of interest. FIG. 5 includes an example avoidance region 515 around the blood vessel 505. The voxels (for example, a fourth set of voxels) located within the avoidance region 515 are not part of the structure of interest. Thus, the electronic processor 205 classifies the voxels located within the avoidance region 515 as belonging to the background class. The values (for example, the intensity values) of the voxels located within the avoidance region 515 may be similar to values of the voxels of the structure of interest. This similarity can cause the voxels located within the avoidance region 515 to negatively impact overall statistical sampling. Thus, in some embodiments, the electronic processor 205 classifies the voxels located within the containment region and outside the inclusion region as belonging to either the foreground class or the background class without statistically sampling the voxels located within the avoidance region 515.

Figure 6A:
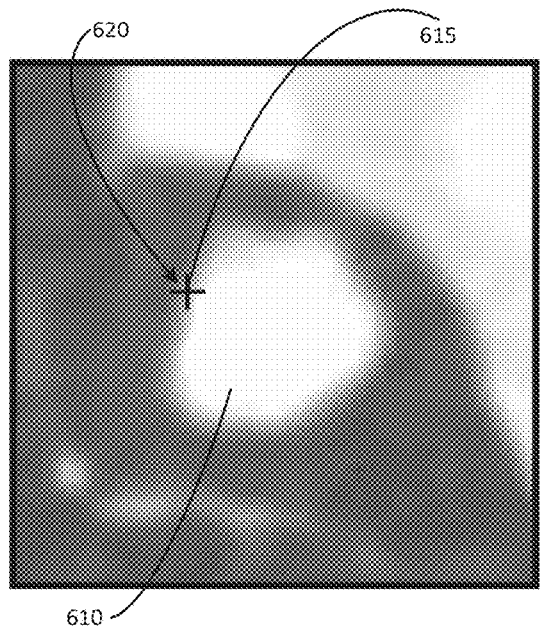
FIGS. 6A through 6D are screen shots of a display illustrating a user inputting a line segment across a structure in a planar medical image, in accordance with some embodiments.
Figure 6B:
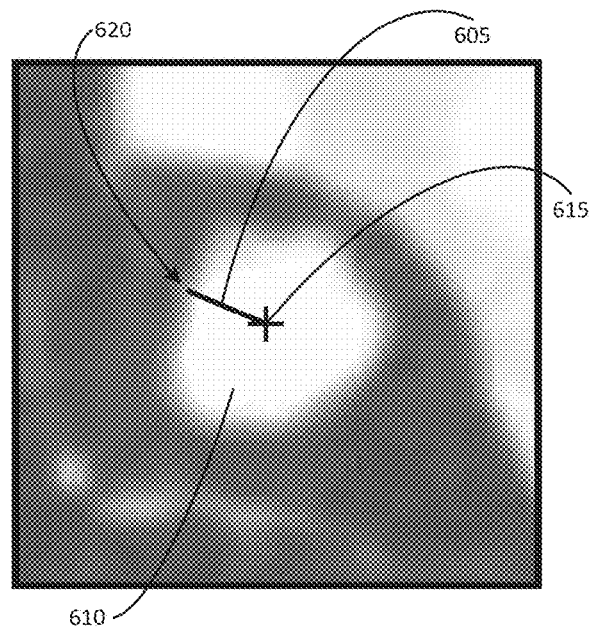
Figure 6C:
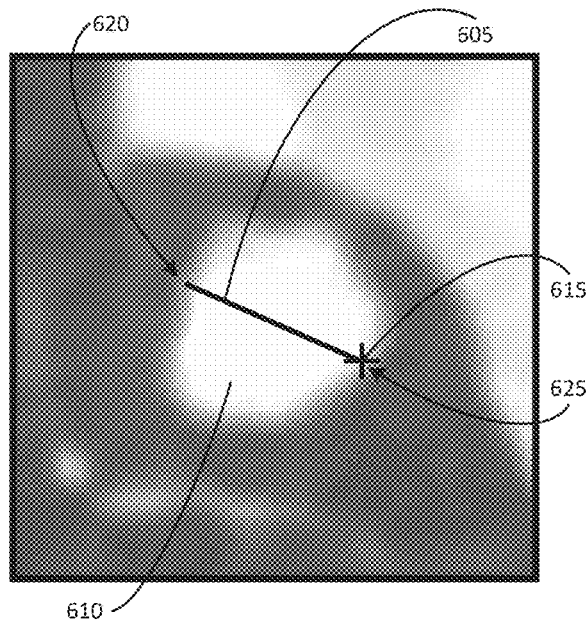
Figure 6D:
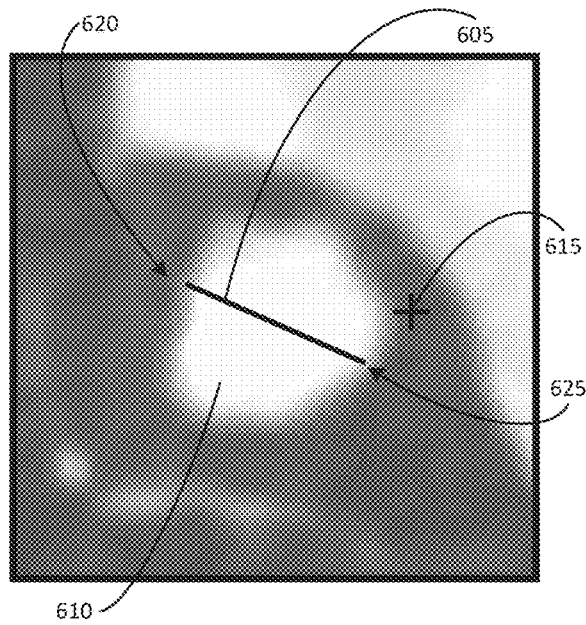

As described herein, in some embodiments, the line segment received via the user interface 225 can be generated by a user dragging a cursor across a structure. FIGS. 6A through 6D are an example series of screen shots of the display 220 illustrating a user inputting a line segment 605 across a structure 610 in a planar medical image. The descriptions of FIGS. 6A through 6D included herein are described as being performed by a user with a mouse. These descriptions are not limiting and merely provide one example implementation. First, the user positions a cursor 615 at a first location 620 in the planar medical image on the border of the structure 610, as illustrated in FIG. 6A. Next, the user presses and holds a button of the mouse while dragging the cursor 615 across the structure 610, as illustrated in FIG. 6B. As the cursor 615 is being dragged, the display 220 displays the line segment 605 as a line between the first location 620 and the current location of the cursor 615. The user moves the cursor 615 to a second location 625 in the planar medical image on the opposite border of the structure 610, as illustrated in FIG. 6C. The user releases the button on the mouse to complete the line segment 605, as illustrated in FIG. 6D.

As described herein, the electronic processor 205 determines 2D contours of the structure using a line segment received via user input received by the user interface 225. Further, the electronic processor 205 determines the inclusion region, the containment region, and the background region based in part on the 2D contours of the structure. As such, the accuracy of the volumetric segmentation techniques described herein improve when user input inputs a line segment that closely represents the long axis. In order to improve the quality line segments input by the user, in some embodiments, the system 200 determines and displays the 2D contours in real-time as the user is drawing the line segment.

Figure 7A:
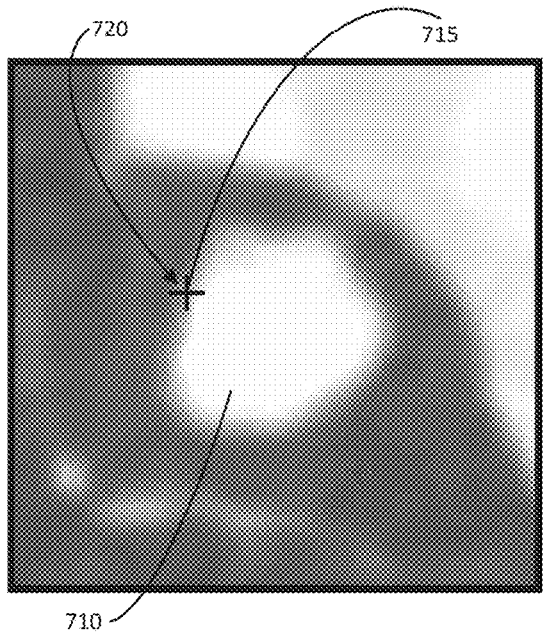
FIGS. 7A through 7C are screen shots of a display illustrating two dimensional (2D) contour generation while a user inputs a line segment across a structure in a planar medical image, in accordance with some embodiments.
Figure 7B:
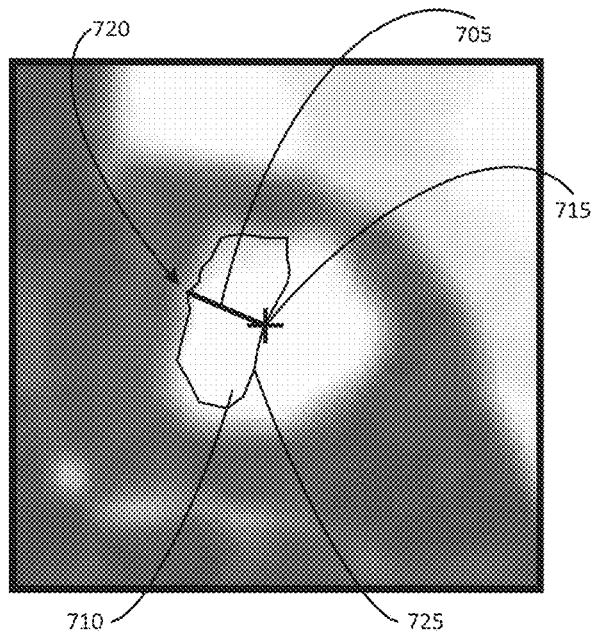
Figure 7C:
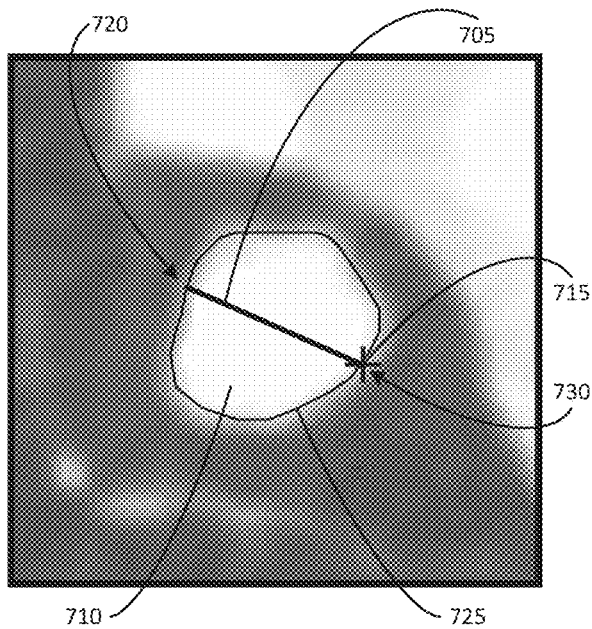

FIGS. 7A through 7C are an example series of screen shots of the display 220 illustrating real-time determination and display of 2D contours while a user inputs a line segment 705 across a structure 710 in a planar medical image. The descriptions of FIGS. 7A through 7C included herein are described as being performed by a user with a mouse. These descriptions are not limiting and merely provide one example implementation. First, the user positions a cursor 715 at a first location 720 in the planar medical image on the border of the structure 710, as illustrated in FIG. 7A. Next, the user presses and holds a button of the mouse while dragging the cursor 715 across the structure 710, as illustrated in FIG. 7B. As the cursor 715 is dragged across the structure 710, the electronic processor 205 determines a 2D contour 725 of the structure 710 based on the line segment 705 between the first location 720 and the current location of the cursor 715 (for example, a third location). The display 220 displays visual indicators of the line segment 705 and the 2D contour 725 on the planar medical image, as illustrated in FIG. 7B. When the cursor 715 is positioned at a location 730 on the opposite border of the structure 710, the 2D contour 725 substantially encompasses the entire structure 710, as illustrated in FIG. 7C. By determining and displaying 2D contours in real-time as the line segment is being drawn, as illustrated in FIGS. 7A through 7C, a user is able to provide a line segment that more closely represents the long axis.

In some situations, the 2D contours determined by the electronic processor 205 using the line segment may not contain the entire structure. The line segment (for example, a first line segment) may not be a good approximation of the long axis, and thus the 2D contours may not include a portion of the structure. In some embodiments, the electronic processor 205 adjusts the 2D contours based on additional user input. For example, in some embodiments, the electronic processor 205 receives additional user input (for example, a second user input) from the user interface 225 indicating a second line segment in a planar medical image. The first line segment and the second line segment may be from the same planar medical image. The second line segment includes, for example, the portion of the structure that is not included in the 2D contour or a second approximation of the long axis. The electronic processor 205 adjusts the 2D contour using the first line segment and the second line segment. In some such embodiments, the electronic processor 205 may determine the inclusion region, the containment region, and the background region using the first line segment, the second line segment, the adjusted 2D contour, or a combination thereof. For example, the inclusion region may embody the adjusted 2D contour. For example, the containment region may be shaped such that its intersection with the planar medical image conforms to the adjusted 2D contour. For example, the background region may be placed by performing statistical clustering of the voxels in the vicinity of the adjusted 2D contour in order to find the clusters that best bracket the probability distribution of the inclusion region. In some embodiments, the electronic processor 205 adds an avoidance region around the adjusted 2D contour. In general, the containment region and the avoidance region remove voxels from consideration during classification that could be distracting because of these voxel's similarity and brightness to the voxels of the target structure. Since it may be difficult to discern the voxels located outside the containment region and the voxels located within the avoidance region by brightness alone, these voxels can be described by spatial position.

In some embodiments, the electronic processor 205 may receive additional user input (for example, a second user input) from the user interface 225 indicating an edit to the 2D contour. Edits to the 2D contour may include, for example, the user dragging a portion of the 2D contour with a cursor or the user drawing a corrected 2D contour with a cursor. In some such embodiments, the electronic processor 205 may determine the inclusion region, the containment region, and the background region using the first line segment, the edit to the 2D contour, or a combination thereof.

As described herein, in some embodiments, the electronic processor 205 determines the inclusion region, the containment region, and the background region using a single line segment in a single planar medical image. In alternate embodiments, the electronic processor 205 determines the inclusion region, the containment region, and the background region using multiple line segments in different planar medical images. For example, the electronic processor 205 may display a first planar medical image and a second planar medical image on the display 220. The second planar medical image is an image slice along a different plane of the 3D volume than the first planar medical image. For example, the first planar medical image may be an image slice along an axial plane of the 3D volume, and second planar medical image may be an image slice along a sagittal plane of the 3D volume. The electronic processor 205 receives a first user input from the user interface 225 indicating a first line segment in the first planar medical image. The electronic processor 205 also receives a second user input from the user interface 225 indicating a second line segment in the second planar medical image. The electronic processor 205 determines the inclusion region, the containment region, and the background region using the first line segment and the second line segment.

In some embodiments, after the 3D contour (for example, a first 3D contour) is determined, the electronic processor 205 may receive additional user input (for example, a second user input) from the user interface 225 indicating an edit to the 3D contour. Edits to the 3D contour may include, for example, the user dragging a portion of the 3D contour with a cursor, the user drawing a corrected 3D contour with a cursor, or alterations to the containment region, the inclusion region, the background region, the long axis, and the short axis. The user may alter one of the containment, inclusion, and background regions, for example, by dragging a portion of a region with a cursor, or by drawing a corrected portion of a region with a cursor. The user may alter the long axis or the short axis, for example, by dragging an endpoint of an axis with a cursor. The electronic processor 205 determines a new inclusion region (for example, a second inclusion region) and a new containment region (for example, a second containment region) using the line segment and the edit to the 3D contour. Using the second inclusion region, the second containment region, and the background region, the electronic processor 205 classify the voxels located within the second containment region as belonging to either the foreground class or the background class. Next, the electronic processor 205 determines a new 3D contour of the structure (for example, a second 3D contour of the structure) based on a border in the 3D volume between the voxels belonging to the foreground class and the voxels belonging to the background class.

Figure 8:
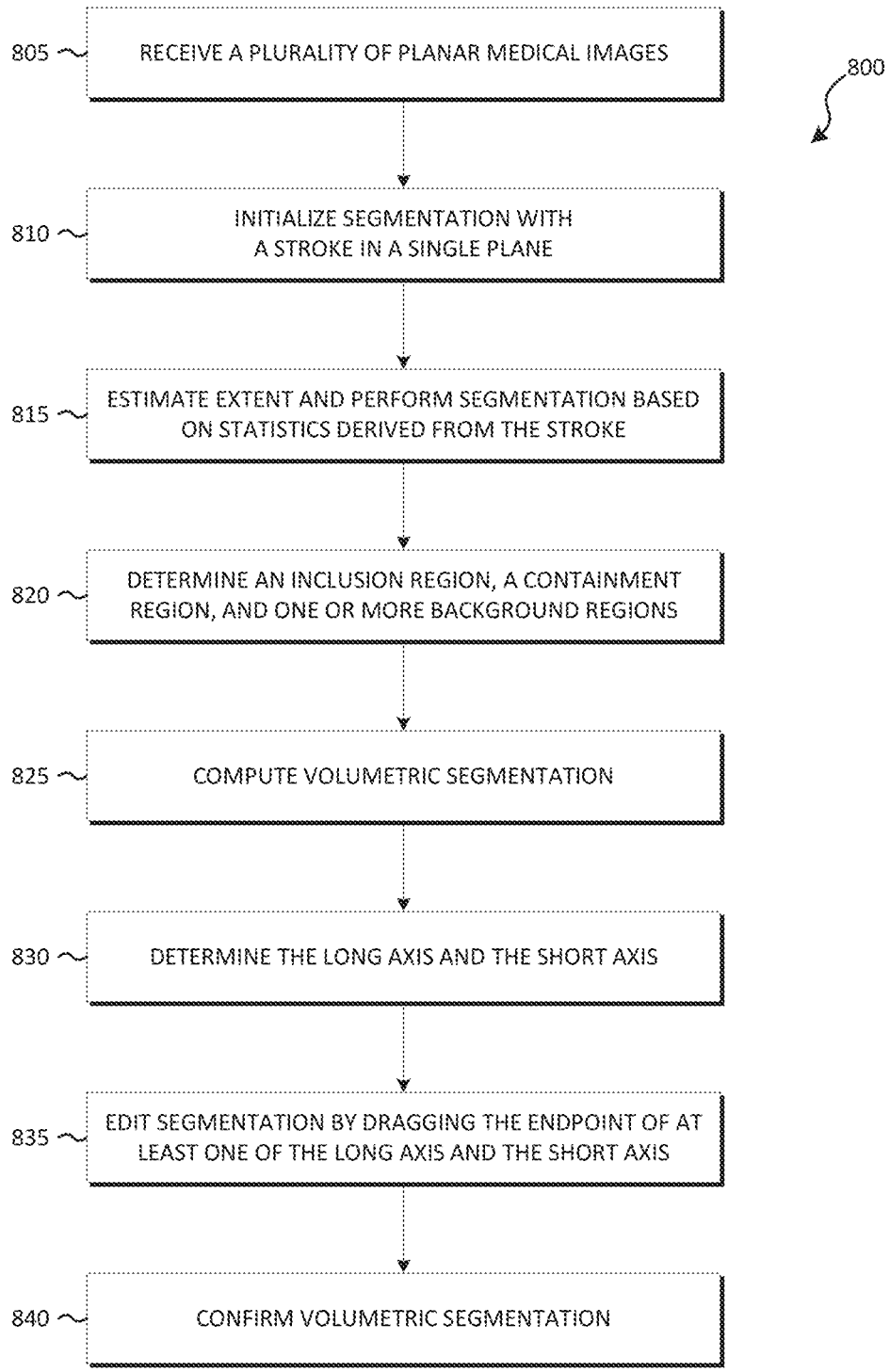
FIG. 8 is a flowchart of a method for segmentation of a foreground structure in a plurality of planar medical images, in accordance with some embodiments.

FIG. 8 illustrates an example method 800 for segmentation of a foreground structure in a plurality of planar medical images. The method 800 is described as being performed by the system 200 and, in particular, the electronic processor 205. However, it should be understood that in some embodiments, portions of the method 800 may be performed by other devices included in the system 200.

At block 805, the electronic processor 205 receives a plurality of planar medical images. The plurality of planar medical images forms a 3D volume that includes a structure. The plurality of planar medical image includes, for example, one or more computed tomography (CT) images, positron emission tomography (PET) images, magnetic resonance imaging (MRI) images, X-ray images, or a combination thereof. In some embodiments, the system 200 imports the plurality of planar medical images from a computer network (for example, a server) or a file system. In some embodiments, the imported medical images includes one or more of a set of CT, PET, multi-spectral MRI images all of which define the Image Pixel and Image Plane module of the DICOM PS 3.3 specification and are assembled to create a 3D rectilinear image volume.

At block 810, segmentation is initialized by a stroke in any one plane, providing an approximate diameter of the region of interest. In some embodiments, a multi-planar reformatting is performed that allows presentation of three image slice planes along the axial, sagittal, and coronal planes. The user interface 225 lets the user scroll to use any of the planar medical images on any of these three planes. The segmentation process can be initiated by either one stroke on any of these planes or by two different strokes, each on a different plane. These strokes provide image pixel brightness and spatial seed points for the segmentation process.

At block 815, the electronic processor 205 estimates the extent of the foreground structure along two other dimensions. In some embodiments, the electronic processor 205 performs a quick segmentation based on statistics derived from the strokes provided at block 810. This can constitute the approximation of the extent along all dimensions.

At block 820, the electronic processor 205 determines an inclusion region, a containment region, and one or more background regions. The inclusion region is smaller than the approximate segmentation and is contained wholly inside it. The containment region is larger than the approximate segmentation region and wholly contains it. The background regions are positioned outside the containment region. The electronic processor 205 searches the plurality of planar medical images prior to the determination of the background regions. In some embodiments, the electronic processor 205 determines a first background region in tissue that is darker, and a second background region in tissue that is brighter. Alternatively, the electronic processor 205 determines background regions in statistically distinct places. In some embodiments, the inclusion region and the containment region are ellipsoidal shapes and the background regions are spherical shapes.

Figure 9:
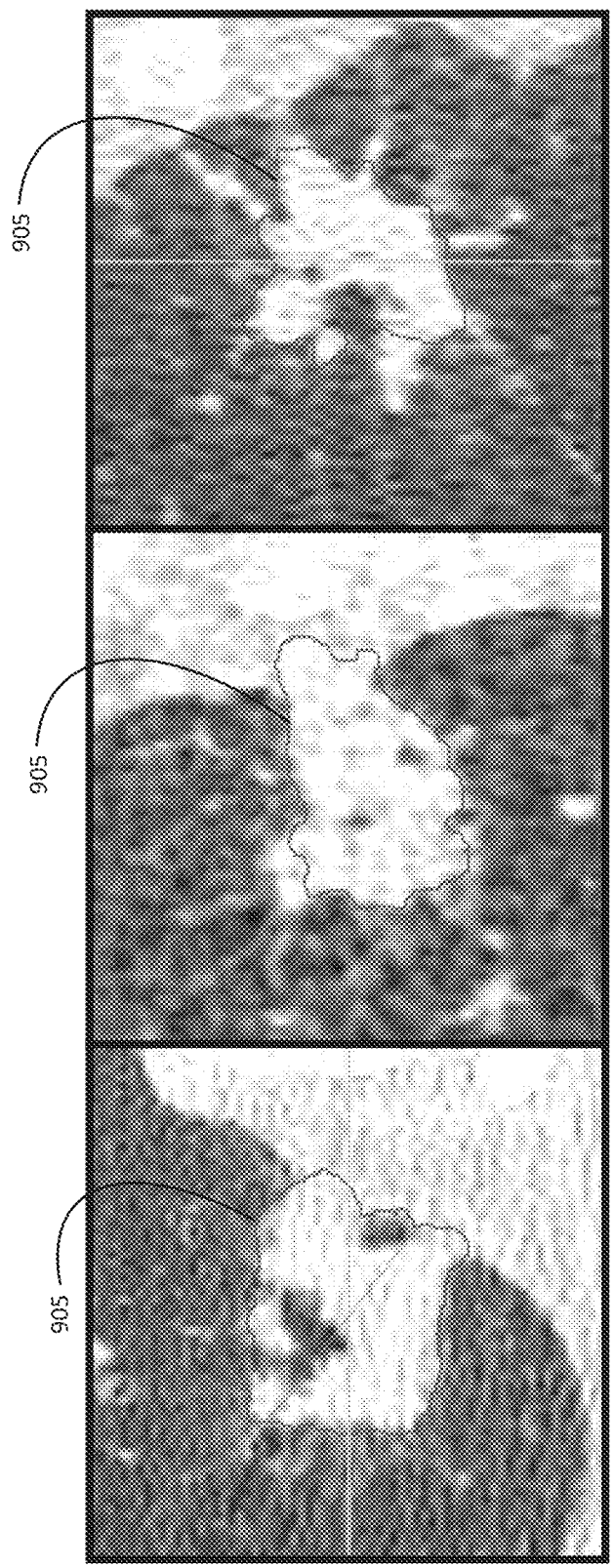
FIG. 9 is a multi-planar view of three image slice planes including two dimensional (2D) contours of a structure, in accordance with some embodiments.
Figure 10:
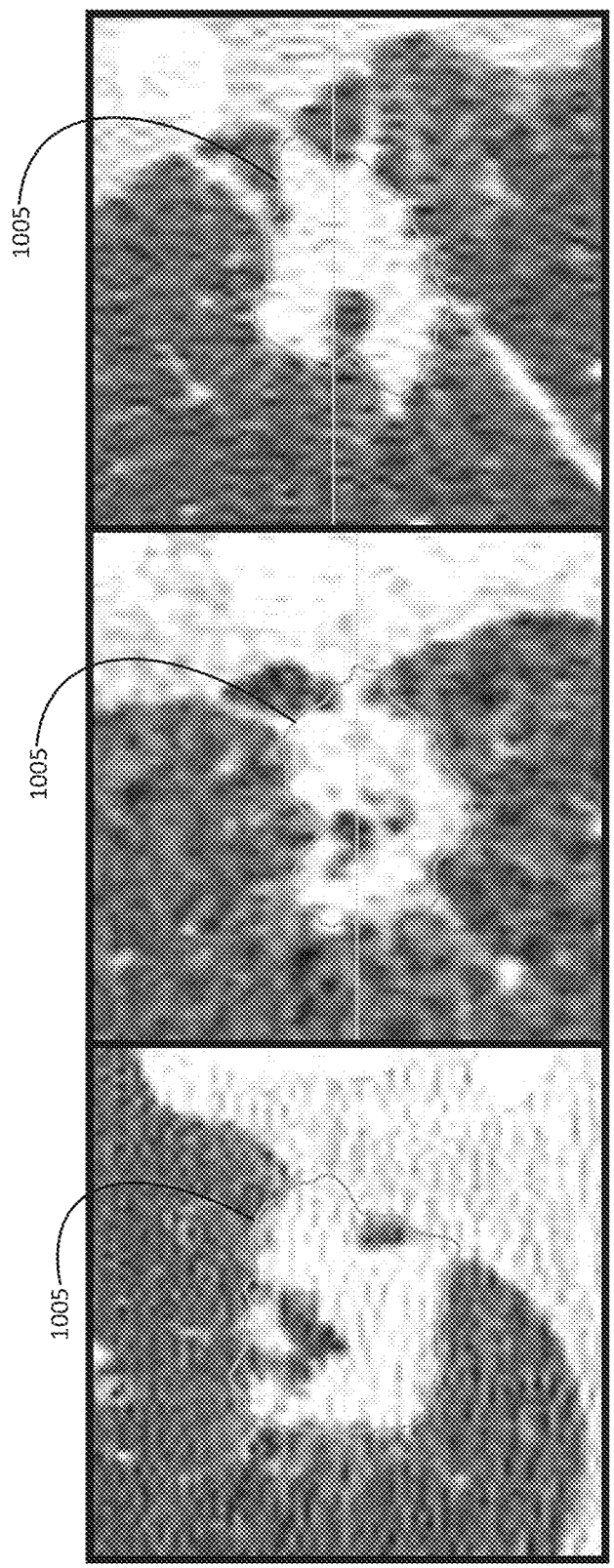
FIG. 10 is a multi-planar view of three image slice planes including three dimensional (3D) contours of a structure, in accordance with some embodiments.

At block 825, the electronic processor 205 computes volumetric segmentation. In some embodiments, the segmentation process performs Bayesian classification wherein prior probabilities are spatially varying and derived from region boundaries and may be a function of the distance from the inclusion region and the containment region. The conditional densities (for example, the likelihoods) may be derived from sampling the voxels within the background and inclusion regions in order to perform Parzen window density estimation. In some embodiments, the electronic processor 205 analyzes multi-spectral images using multi-dimensional Bayesian classification such that there are two categories (i.e., background and foreground), and there are as many dimensions of feature space as there are spectrums. Each plurality of planar medical images can be sampled inside the inclusion region and the background region. One classification, given all series as multi-variate input, can be performed inside the containment region. In some embodiments, the electronic processor 205 computes 2D contours in real time and computes 3D contours in the background. In such embodiments, the 3D contours are displayed on the display 220 only after the electronic processor 205 finishes calculating the 3D contours. FIG. 9 is an example screen shot of the display 220 illustrating an example multi-planar view of three image slice planes along the axial, sagittal, and coronal planes with the 2D contours 905 displayed. FIG. 10 is an example screen shot of the display 220 illustrating an example multi-planar view of three image slice planes with the calculated 3D contours 1005 displayed.

At block 830, the electronic processor 205 determines the long axis and the short axis. In some embodiments, the electronic processor 205 identifies the planar medical image that contains the long axis and displays that planar medical image to the user on the display 220. Additionally, as the user scrolls through the planar medical images, the electronic processor 205 updates and displays the long axis and the short axis on any of these planar medical images.

Figure 11:
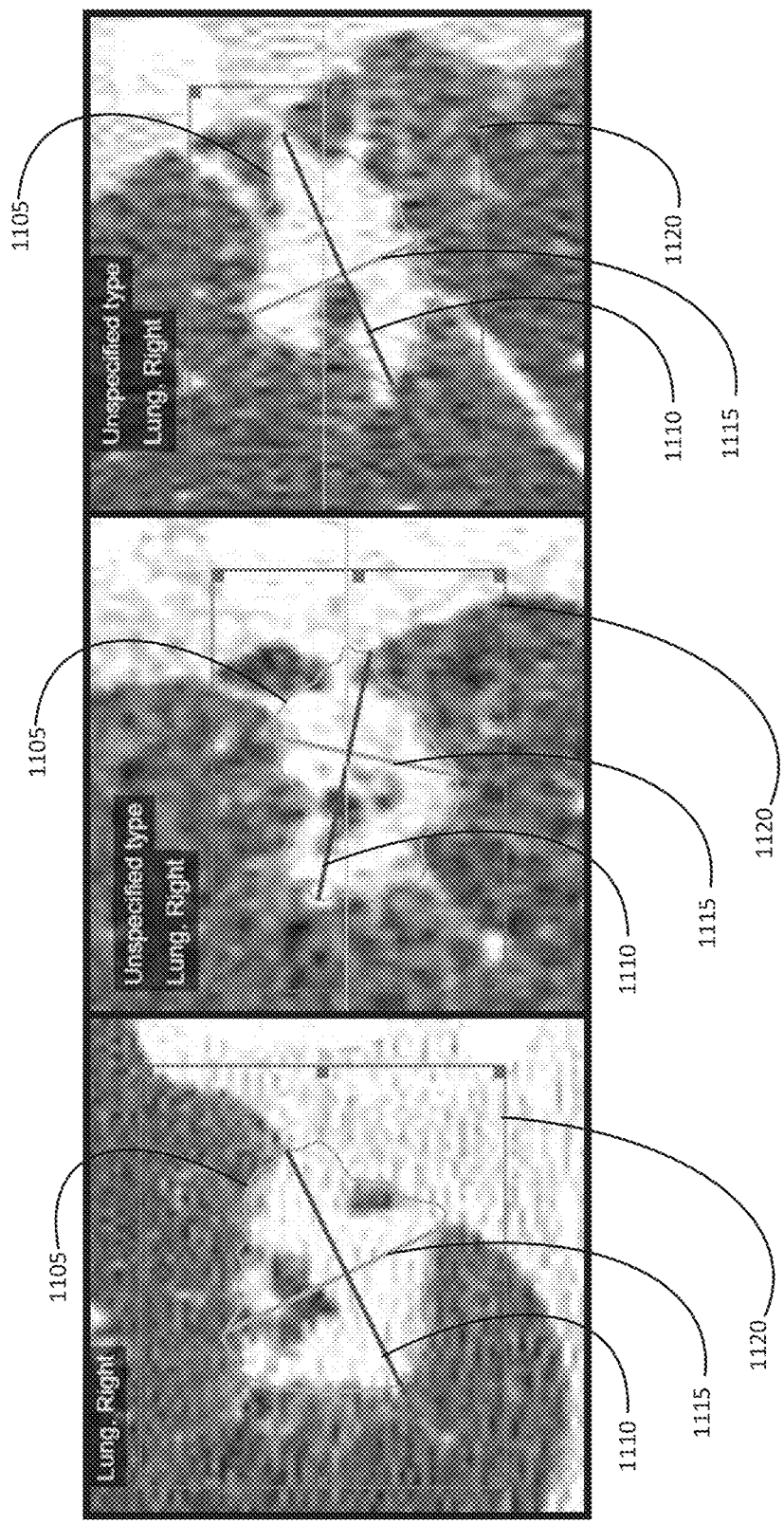
FIG. 11 is a multi-planar view of three image slice planes including bounding boxes, in accordance with some embodiments.

At block 835, the volumetric segmentation is edited by dragging an endpoint of the long axis or the short axis. For example, the user can select the end point of the long axis or the short axis on the display 220 and drag the end point to edit the volumetric segmentation. The act of dragging the end points creates a deformation of the containment region and the inclusion region, and thus, alters the volumetric segmentation. The volumetric segmentation can also by edited by the user dragging a side of a bounding box that, in some embodiments, is displayed on the display 220 in a planar medical image. FIG. 11 is an example screen shot of the display 220 illustrating an example multi-planar view of three image slice planes with a 3D contour 1105, a long axis 1110, a short axis 1115, and a bounding box 1120 displayed. The bounding box contains the extent of the segmentation of the foreground structure. Altering the size of the bounding box contributes to the deformation of the containment region, thus affecting the segmentation. In some embodiments, movement of the bounding box is constrained to not impinge on the inclusion region.

At block 840, the volumetric segmentation is confirmed, for example, by the user. The user evaluates the 3D contours of the segmentation. If the user agrees, the user is prompted to confirm it and the system 200 stores the new segmentation, for example, in the data storage 215. One reason to store the volumetric segmentation is to compute various quantitative metrics to be used for Radiomics. If the user disagrees, the system 200 stores the long axis measurement and/or the short axis measurement, for example, in the data storage 215.

In some embodiments, normal organs can be segmented reliably and automatically without any intervention. They can be pre-computed before the user starts interacting with the system 200 to segment the lesions. The segmentation methods described herein can be organ specific and organ-aware. In some embodiments, the electronic processor 205 detects organs in planar medical images. In other words, the electronic processor 205 can determine the organ in which a lesion lies. In some embodiments, the electronic processor 205 accounts for known lesions during segmentation. For example, lymph nodes are known to be spherical in shape and the segmentation can be constrained to be rounded. RECIST guidelines treat the short axis differently for lymph nodes, so automatic organ identification saves time and manual data entry for the user. In some embodiments, the electronic processor 205 excludes the lung vessels from lung lesions. For example, vessels can be identified by their brightness, connectedness, and tubular shape, as measured by Eigen-analysis. In some embodiments, the lung vessel segmentation will also be included in normal organ segmentation. Inflammation and bullae are additional examples of lung-specific structures than can be considered for removal from the structure. Inflammation, often precipitated by the lesion, may be excluded from the lesion volume. Inflammation may be identified by brightness, shape, and position as emanations relative to solid mass. Lung nodules may contain air bubbles, involve bronchioles, or grow adjacent to bullae. Radiologists may decide whether to include each air pocket on a case-by-case basis. For example, bubbles whose outlines correspond significantly with the outline of the lesion could be included, whereas bubbles whose outlines show little overlap could be excluded.

In some embodiments, the methods provided herein are performed by a software executed by a server, and a user may access and interact with the software application using a computing device. Also, in some embodiments, functionality provided by the software application may be distributed between a software application executed by a local device and a software application executed by another electronic process or device (for example, a server) external to the local device.

In the foregoing specification, specific embodiments have been described. However, one of ordinary skill in the art appreciates that various modifications and changes may be made without departing from the scope of the disclosure as set forth in the claims below. Accordingly, the specification and figures are to be regarded in an illustrative rather than a restrictive sense, and all such modifications are intended to be included within the scope of present teachings.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element preceded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. A device or structure that is "configured" in a certain way is configured in at least that way, but may also be configured in ways that are not listed.

Various features and advantages of some embodiments are set forth in the following claims.

What is claimed is:

1. A method for volumetric segmentation of a structure in a plurality of planar medical images, the method comprising:
   receiving, at an electronic processor, the plurality of planar medical images, wherein the plurality of planar medical images form a three dimensional (3D) volume including the structure;
   displaying, on a display, a first planar medical image from the plurality of planar medical images;
   detecting, with a user interface, a user selection at a first location in the first planar medical image;
   detecting, with the user interface, a user deselection at a second location in the first planar medical image, wherein the second location is different from the first location;
   prior to detecting the user deselection,
      receiving, with the user interface, a third location in the first planar medical image, wherein the third location is different from the first location and the second location;
      determining, with the electronic processor, a first two dimensional (2D) contour of the structure using a first single straight line segment between the third location and the first location;
      re-displaying, on the display, the first planar medical image with visual indicators of the first single straight line segment and the first 2D contour of the structure;
   receiving, with the user interface, the second location after receiving the third location;
      determining, with the electronic processor, a second 2D contour of the structure using a second single straight line segment between the second location and the first location; and
      re-displaying, on the display, the first planar medical image with visual indicators of the second single straight line segment and the second 2D contour of the structure; and
   after detecting the user deselection,
      determining, with the electronic processor, an inclusion region of the 3D volume using the second single straight line segment, wherein the inclusion region consists of a portion of the structure;
      determining, with the electronic processor, a containment region of the 3D volume using the second single straight line segment, wherein the containment region includes the structure;
      determining, with the electronic processor, a background region of the 3D volume using the second single straight line segment, wherein the background region excludes the structure;
      determining, with the electronic processor, a 3D contour of the structure using the inclusion region, the containment region, and the background region;
      determining, with the electronic processor, a long axis of the structure using the 3D contour of the structure; and
      outputting, with the electronic processor, a dimension of the long axis of the structure.

2. The method of claim 1, wherein the dimension is a first dimension, wherein the method further comprising
   determining, with the electronic processor, a short axis of the structure using the 3D contour of the structure; and
   outputting, with the electronic processor, a second dimension of the short axis of the structure.

3. The method of claim 1, further comprising
   identifying, with the electronic processor, a second planar medical image from the plurality of planar medical images that includes the long axis of the structure; and
   displaying, on the display, the second planar medical image with a visual indicator of the long axis.

4. The method of claim 1, further comprising
   classifying, with the electronic processor, a first set of voxels located within the inclusion region as belonging to a foreground class;
   classifying, with the electronic processor, a second set of voxels located within the background region as belonging to a background class;
   statistically sampling, with the electronic processor, the first set of voxels and the second set of voxels to classify a third set of voxels located within the containment region and outside the inclusion region as belonging to either the foreground class or the background class;
   determining, with the electronic processor, a border in the 3D volume between the third set of voxels belonging to the foreground class and the third set of voxels belonging to the background class; and
   determining, with the electronic processor, the 3D contour of the structure based on the border in the 3D volume.

5. The method of claim 4, further comprising
   classifying, with the electronic processor, the third set of voxels as belonging to either the foreground class or the background class using Bayesian classification.

6. The method of claim 4, further comprising
determining, with the electronic processor, an avoidance region of the 3D volume, wherein the avoidance region does not include the structure;
classifying, with the electronic processor, a fourth set of voxels within the avoidance region as belonging to the background class; and
classifying, with the electronic processor, the third set of voxels as belonging to either the foreground class or the background class without statistically sampling the fourth set of voxels.

7. The method of claim 1, wherein determining, with the electronic processor, the 3D contour of the structure using the inclusion region, the containment region, and the background region including
statistically sampling, with the electronic processor, the inclusion region and the background region to determine the 3D contour of the structure within the containment region.

8. The method of claim 1, wherein determining, with the electronic processor, the containment region using the second single straight line segment including
determining, with the electronic processor, three 2D contours of the structure using the second single straight line segment, wherein each of the three 2D contours of the structure is located in a different plane of the 3D volume, and
determining, with the electronic processor, the containment region as an ellipsoid in the 3D volume that completely encompasses the three 2D contours of the structure.

9. The method of claim 8, wherein determining, with the electronic processor, the three 2D contours of the structure using the second single straight line segment including
statistically sampling, with the electronic processor, along the second single straight line segment to determine a probability distribution for image brightness, and
determining, with the electronic processor, the three 2D contours of the structure based on the probability distribution for image brightness.

10. The method of claim 8, wherein determining, with the electronic processor, the three 2D contours of the structure using the second single straight line segment including
determining, with the electronic processor, boundary profiles based on the end points of the second single straight line segment, and
sampling, with the electronic processor, the boundary profiles to determine the three 2D contours of the structure.

11. A system for determining volumetric segmentation of a structure in a plurality of planar medical images, the system comprising:
a display;
a user interface; and
an electronic processor configured to
receive the plurality of planar medical images, wherein the plurality of planar medical images form a three dimensional (3D) volume including the structure and a plurality of voxels,
display, on the display, a first planar medical image from the plurality of planar medical images,
detect, with the user interface, a user selection at a first location in the first planar medical image,
detect, with the user interface, a user deselection at a second location in the first planar medical image, wherein the second location is different from the first location,
prior to detecting the user deselection,
receive, with the user interface, a third location in the first planar medical image, wherein the third location is different from the first location and the second location,
determine a first two dimensional (2D) contour of the structure using a first single straight line segment between the third location and the first location,
re-display, on the display, the first planar medical image with visual indicators of the first single straight line segment and the first 2D contour of the structure,
receive, with the user interface, the second location after receiving the third location,
determine a second 2D contour of the structure using a second single straight line segment between the second location and the first location, and
re-display, on the display, the first planar medical image with visual indicators of the second single straight line segment and the second 2D contour of the structure, and
after detecting the user deselection,
determine an inclusion region of the 3D volume using the second single straight line segment, wherein the inclusion region consists of a portion of the structure,
determine a containment region of the 3D volume using the second single straight line segment, wherein the containment region includes the structure,
determine a background region of the 3D volume using the single second straight line segment, wherein the background region excludes the structure,
classify the voxels located within the containment region as belonging to either a foreground class or a background class using the inclusion region, the containment region, and the background region,
determine a 3D contour of the structure based on a border in the 3D volume between the voxels belonging to the foreground class and the voxels belonging to the background class,
determine a long axis of the structure using the 3D contour of the structure, and
output a dimension of the long axis of the structure.

12. The system of claim 11, wherein the dimension is a first dimension, wherein the electronic processor is further configured to
determine a short axis of the structure using the 3D contour of the structure, and
output a second dimension of the short axis of the structure.

13. The system of claim 11, wherein the electronic processor is further configured to
identify a second planar medical image from the plurality of planar medical images that includes the long axis of the structure, and
display, on the display, the second planar medical image with a visual indicator of the long axis.

14. The system of claim 11, wherein the electronic processor is further configured to
classify the voxels located within the inclusion region as belonging to the foreground class,
classify the voxels located within the background region as belonging to the background class, and
statistically sample the voxels locating within the inclusion region and the voxels located within the background region to classify the voxels located within the containment region and outside the inclusion region as belonging to either the foreground class or the background class.

15. The system of claim 14, wherein the electronic processor is further configured to classify each of the voxels located within the containment region and outside the inclusion region as belonging to either the foreground class or the background class using Bayesian classification.

16. The system of claim 14, wherein the electronic processor is further configured to
determine an avoidance region of the 3D volume, wherein the avoidance region does not include the structure,
classify the voxels located within the avoidance region as belonging to the background class, and
classify the voxels located within the containment region and outside the inclusion region as belonging to either the foreground class or the background class without statistically sampling the voxels located within the avoidance region.

17. The system of claim 11, wherein the electronic processor is further configured to
receive, with the user interface, a user input indicating a third single straight line segment in the first planar medical image,
adjust the second 2D contour of the structure using the third single straight line segment and the second single straight line segment,
determine the inclusion region of the 3D volume using the third single straight line segment, the second single straight line segment, and the adjusted second 2D contour of the structure,
determine the containment region of the 3D volume using the third single straight line segment, the second single straight line segment, and the adjusted second 2D contour of the structure, and
determine the background region of the 3D volume using the third single straight line segment, the second single straight line segment, and the adjusted second 2D contour of the structure.

18. The system of claim 11, wherein the electronic processor is further configured to
receive, with the user interface, a user input indicating an edit to the second 2D contour of the structure,
determine the inclusion region of the 3D volume using the second single straight line segment and the edit to the second 2D contour of the structure,
determine the containment region of the 3D volume using the second single straight line segment and the edit to the second 2D contour of the structure, and
determine the background region of the 3D volume using the second single straight line segment and the edit to the second 2D contour of the structure.

19. The system of claim 11, wherein the electronic processor is further configured to
display, on the display, a second planar medical image from the plurality of planar medical images, wherein a first plane of the first planar medical image is different from a second plane of the second planar medical image,
receive, with the user interface, a user input indicating a third single straight line segment in the second planar medical image,
determine the inclusion region of the 3D volume using the third single straight line segment and the second single straight line segment,
determine the containment region of the 3D volume using the third single straight line segment and the second single straight line segment, and
determine the background region of the 3D volume using the third single straight line segment and the second single straight line segment.

20. The system of claim 11, wherein the 3D contour of the structure is a first 3D contour of the structure, wherein the electronic processor is further configured to
re-display, on the display, the first planar medical image with a visual indicator of the first 3D contour of the structure,
receive, with the user interface, a user input indicating an edit to the first 3D contour of the structure,
determine a second inclusion region of the 3D volume using the second single straight line segment and the edit to the first 3D contour of the structure,
determine a second containment region of the 3D volume using the second single straight line segment and the edit to the first 3D contour of the structure,
classify the voxels located within the second containment region as belonging to either the foreground class or the background class using the second inclusion region, the second containment region, and the background region, and
determine a second 3D contour of the structure based on a second border in the 3D volume between the voxels belonging to the foreground class and the voxels belonging to the background class.

21. A non-transitory machine-readable storage medium for use in connection with a system comprising an electronic processor, a display, and a user interface, the non-transitory machine-readable storage medium comprising instructions that when executed by the electronic processor cause the electronic processor to
receive a plurality of planar medical images, wherein the plurality of planar medical images form a three dimensional (3D) volume including a structure;
display, on the display, a first planar medical image from the plurality of planar medical images;
detect, with the user interface, a user selection at a first location in the first planar medical image;
detect, with the user interface, a user deselection at a second location in the first planar medical image, wherein the second location is different from the first location;
prior to detecting the user deselection,
receive, with the user interface, a third location in the first planar medical image, wherein the third location is different from the first location and the second location;
determine a first two dimensional (2D) contour of the structure using a first single straight line segment between the third location and the first location;
re-display, on the display, the first planar medical image with visual indicators of the first single straight line segment and the first 2D contour of the structure;
receive, with the user interface, the second location after receiving the third location;
determine a second 2D contour of the structure using a second single straight line segment between the second location and the first location; and re-display, on the display, the first planar medical image with visual indicators of the second single straight line segment and the second 2D contour of the structure; and after detecting the user deselection,
- determine an inclusion region of the 3D volume using the second single straight line segment, wherein the inclusion region consists of a portion of the structure;
- determine a containment region of the 3D volume using the second single straight line segment, wherein the containment region includes the structure;
- determine a background region of the 3D volume using the second single straight line segment, wherein the background region excludes the structure;
- determine a 3D contour of the structure using the inclusion region, the containment region, and the background region;
- determine a long axis of the structure using the 3D contour of the structure; and
- output a dimension of the long axis of the structure.

22. The non-transitory machine-readable storage medium of claim 21, wherein the dimension is a first dimension, wherein the instructions further cause the electronic processor to
- determine a short axis of the structure using the 3D contour of the structure; and output a second dimension of the short axis of the structure.

\* \* \* \* \*